(12) United States Patent
Ichinohe et al.

(10) Patent No.: US 8,535,375 B2
(45) Date of Patent: Sep. 17, 2013

(54) INTRAOCULAR LENS INSERTION DEVICE

(75) Inventors: Takashi Ichinohe, Honjo (JP); Kenji Someya, Kasukabe (JP); Kazunori Kudoh, Saku (JP)

(73) Assignee: Hoya Corporation, Tokyo (JP)

( * ) Notice: Subject to any disclaimer, the term of this patent is extended or adjusted under 35 U.S.C. 154(b) by 0 days.

(21) Appl. No.: 13/244,452

(22) Filed: Sep. 24, 2011

(65) Prior Publication Data

US 2012/0071887 A1 Mar. 22, 2012

Related U.S. Application Data

(62) Division of application No. 12/602,454, filed as application No. PCT/JP2009/059995 on May 30, 2008, now Pat. No. 8,475,528.

(30) Foreign Application Priority Data

May 30, 2007 (JP) ................................. 2007-144263

(51) Int. Cl.
*A61F 2/16* (2006.01)
*A61F 9/00* (2006.01)

(52) U.S. Cl.
USPC ........................................ 623/6.12; 606/107

(58) Field of Classification Search
USPC ................. 606/107; 623/6.23, 6.12
See application file for complete search history.

(56) References Cited

U.S. PATENT DOCUMENTS

| | | |
|---|---|---|
| 2,761,446 A | 9/1956 | Reed |
| 4,205,747 A | 6/1980 | Gilliam et al. |
| 4,269,307 A | 5/1981 | LaHaye |
| 4,423,809 A | 1/1984 | Mazzocco |
| 4,573,998 A | 3/1986 | Mazzocco |
| 4,608,049 A | 8/1986 | Kelman |
| 4,634,423 A | 1/1987 | Bailey |
| 4,681,102 A | 7/1987 | Bartell |
| 4,697,697 A | 10/1987 | Graham et al. |
| 4,699,140 A | 10/1987 | Holmes |
| 4,702,244 A | 10/1987 | Mazzocco |
| 4,715,373 A | 12/1987 | Mazzocco et al. |
| 4,747,404 A | 5/1988 | Jampel et al. |
| 4,750,498 A | 6/1988 | Graham |
| 4,759,359 A | 7/1988 | Willis et al. |
| 4,763,650 A | 8/1988 | Hauser |
| 4,765,329 A | 8/1988 | Cumming et al. |
| 4,769,034 A | 9/1988 | Poley |

(Continued)

FOREIGN PATENT DOCUMENTS

| | | |
|---|---|---|
| DE | 3610925 | 10/1987 |
| DE | 4110278 | 10/1992 |

(Continued)

*Primary Examiner* — Kathleen Holwerda
*Assistant Examiner* — Sarah W Aleman
(74) *Attorney, Agent, or Firm* — Henricks, Slavin, Holmes LLP

(57) ABSTRACT

An intraocular lens insertion device capable of folding an intraocular lens into a predetermined shape without giving a local stress to the intraocular lens. The intraocular lens insertion device 2 may include a lens disposing part 15 for disposing an intraocular lens 4, a slider 7 for pushing out the intraocular lens 4, a plunger 8 for further pushing out the intraocular lens pushed out by the slider 7, a transition part 31 for deforming the intraocular lens 4 pushed out by the slider and the plunger, and a nozzle 32 for ejecting out the deformed intraocular lens 4.

16 Claims, 21 Drawing Sheets

(56) References Cited

U.S. PATENT DOCUMENTS

| | | |
|---|---|---|
| 4,781,719 A | 11/1988 | Kelman |
| 4,787,904 A | 11/1988 | Severin |
| 4,819,631 A | 4/1989 | Poley |
| 4,834,094 A | 5/1989 | Patton |
| 4,836,201 A | 6/1989 | Patton |
| 4,862,885 A | 9/1989 | Cumming |
| 4,880,000 A | 11/1989 | Holmes et al. |
| 4,919,130 A | 4/1990 | Stoy et al. |
| 4,934,363 A | 6/1990 | Smith et al. |
| 4,955,889 A | 9/1990 | Van Gent |
| 4,976,716 A | 12/1990 | Cumming |
| 4,988,352 A | 1/1991 | Poley |
| 4,994,028 A | 2/1991 | Leonard et al. |
| 5,066,297 A | 11/1991 | Cumming |
| 5,098,439 A | 3/1992 | Hill et al. |
| 5,123,905 A | 6/1992 | Kelman |
| 5,139,501 A | 8/1992 | Klaas |
| 5,171,241 A | 12/1992 | Buboltz et al. |
| 5,176,686 A | 1/1993 | Poley |
| 5,190,552 A * | 3/1993 | Kelman .................. 606/107 |
| 5,190,553 A | 3/1993 | Kanert et al. |
| 5,222,972 A | 6/1993 | Hill et al. |
| 5,242,450 A | 9/1993 | McDonald |
| 5,259,395 A | 11/1993 | Li |
| 5,275,604 A | 1/1994 | Rheinish |
| 5,281,227 A | 1/1994 | Sussman |
| 5,304,182 A | 4/1994 | Rheinish |
| 5,354,333 A | 10/1994 | Kammann et al. |
| 5,395,378 A | 3/1995 | McDonald |
| 5,425,734 A | 6/1995 | Blake |
| 5,454,818 A | 10/1995 | Hambleton et al. |
| 5,468,246 A | 11/1995 | Blake |
| 5,474,562 A | 12/1995 | Orchowski et al. |
| 5,494,484 A | 2/1996 | Feingold |
| 5,496,328 A | 3/1996 | Nakajima et al. |
| 5,499,987 A | 3/1996 | Feingold |
| 5,562,676 A | 10/1996 | Brady et al. |
| 5,571,113 A | 11/1996 | McDonald |
| 5,578,042 A | 11/1996 | Cumming |
| 5,582,613 A | 12/1996 | Brady |
| 5,582,614 A | 12/1996 | Feingold |
| 5,584,304 A | 12/1996 | Brady |
| 5,616,148 A | 4/1997 | Eagles et al. |
| 5,620,450 A | 4/1997 | Eagles et al. |
| 5,643,275 A | 7/1997 | Blake |
| 5,643,276 A | 7/1997 | Zaleski |
| 5,645,534 A | 7/1997 | Chanoch |
| 5,653,715 A | 8/1997 | Reich et al. |
| 5,653,753 A | 8/1997 | Brady et al. |
| 5,702,402 A | 12/1997 | Brady |
| 5,702,441 A | 12/1997 | Zhou |
| 5,716,364 A | 2/1998 | Makker et al. |
| 5,728,075 A | 3/1998 | Levander |
| 5,728,102 A | 3/1998 | Feingold et al. |
| 5,735,858 A | 4/1998 | Makker et al. |
| 5,766,181 A | 6/1998 | Chambers et al. |
| 5,772,666 A | 6/1998 | Feingold |
| 5,772,667 A | 6/1998 | Blake |
| 5,776,138 A | 7/1998 | Vidal et al. |
| 5,800,442 A | 9/1998 | Wolf et al. |
| 5,803,925 A | 9/1998 | Yang et al. |
| 5,807,400 A | 9/1998 | Chambers et al. |
| 5,810,833 A | 9/1998 | Brady et al. |
| 5,810,834 A | 9/1998 | Heyman |
| 5,860,984 A | 1/1999 | Chambers et al. |
| 5,860,986 A | 1/1999 | Reich et al. |
| 5,868,751 A | 2/1999 | Feingold |
| 5,868,752 A | 2/1999 | Makker et al. |
| 5,873,879 A | 2/1999 | Figueroa et al. |
| 5,876,406 A | 3/1999 | Wolf |
| 5,876,407 A | 3/1999 | Makker et al. |
| 5,876,440 A | 3/1999 | Feingold |
| 5,891,152 A | 4/1999 | Feingold |
| 5,902,307 A | 5/1999 | Feingold et al. |
| 5,919,197 A | 7/1999 | McDonald |
| 5,921,989 A | 7/1999 | Deacon et al. |
| 5,928,245 A | 7/1999 | Wolf et al. |
| 5,941,886 A | 8/1999 | Feingold |
| 5,942,277 A | 8/1999 | Makker et al. |
| 5,944,725 A | 8/1999 | Cicenas |
| 5,947,974 A | 9/1999 | Brady et al. |
| 5,947,975 A * | 9/1999 | Kikuchi et al. ............... 606/107 |
| 5,957,748 A | 9/1999 | Ichiha |
| 6,001,107 A | 12/1999 | Feingold |
| 6,010,510 A | 1/2000 | Brown |
| 6,022,358 A | 2/2000 | Wolf et al. |
| 6,048,348 A | 4/2000 | Chambers et al. |
| 6,051,000 A | 4/2000 | Heyman |
| 6,056,757 A | 5/2000 | Feingold et al. |
| 6,056,758 A | 5/2000 | Vidal et al. |
| 6,059,791 A | 5/2000 | Chambers |
| 6,074,397 A | 6/2000 | Chambers et al. |
| 6,083,230 A | 7/2000 | Makker et al. |
| 6,093,193 A | 7/2000 | Makker et al. |
| 6,129,733 A | 10/2000 | Brady et al. |
| 6,142,999 A | 11/2000 | Brady et al. |
| 6,143,000 A | 11/2000 | Feingold |
| 6,162,229 A | 12/2000 | Feingold et al. |
| 6,174,315 B1 | 1/2001 | Chambers et al. |
| 6,214,015 B1 | 4/2001 | Reich et al. |
| 6,241,737 B1 | 6/2001 | Feingold |
| 6,248,111 B1 | 6/2001 | Glick et al. |
| 6,251,114 B1 | 6/2001 | Farmer et al. |
| 6,254,607 B1 | 7/2001 | Makker et al. |
| 6,267,768 B1 | 7/2001 | Deacon et al. |
| 6,283,975 B1 | 9/2001 | Glick et al. |
| 6,283,976 B1 | 9/2001 | Portney |
| 6,312,433 B1 | 11/2001 | Butts |
| 6,334,862 B1 | 1/2002 | Vidal et al. |
| 6,336,932 B1 | 1/2002 | Figueroa et al. |
| 6,355,046 B2 | 3/2002 | Kikuchi et al. |
| 6,371,960 B2 | 4/2002 | Heyman et al. |
| 6,386,357 B1 | 5/2002 | Egawa |
| 6,387,101 B1 | 5/2002 | Butts et al. |
| 6,398,788 B1 | 6/2002 | Makker et al. |
| 6,406,481 B2 | 6/2002 | Feingold et al. |
| 6,428,545 B2 | 8/2002 | Portney |
| 6,447,519 B1 | 9/2002 | Brady et al. |
| 6,447,520 B1 | 9/2002 | Ott et al. |
| 6,468,282 B2 | 10/2002 | Kikuchi et al. |
| 6,471,708 B2 | 10/2002 | Green |
| 6,491,697 B1 | 12/2002 | Clark et al. |
| 6,497,708 B1 | 12/2002 | Cumming |
| 6,500,181 B1 | 12/2002 | Portney |
| 6,506,195 B2 | 1/2003 | Chambers et al. |
| 6,537,283 B2 | 3/2003 | Van Nay |
| 6,540,754 B2 | 4/2003 | Brady |
| 6,554,839 B2 | 4/2003 | Brady |
| 6,558,395 B2 * | 5/2003 | Hjertman et al. ............. 606/107 |
| 6,607,537 B1 | 8/2003 | Binder |
| 6,629,979 B1 | 10/2003 | Feingold |
| 6,666,871 B2 | 12/2003 | Kikuchi et al. |
| 6,679,891 B2 | 1/2004 | Makker et al. |
| 6,685,740 B2 | 2/2004 | Figueroa et al. |
| 6,712,848 B1 | 3/2004 | Wolf et al. |
| 6,723,104 B2 | 4/2004 | Ott |
| 6,733,507 B2 | 5/2004 | McNicholas et al. |
| 6,793,674 B2 | 9/2004 | Zapata |
| 6,858,033 B2 | 2/2005 | Kobayashi |
| 6,921,405 B2 | 7/2005 | Feingold et al. |
| 6,923,815 B2 * | 8/2005 | Brady et al. .................. 606/107 |
| 6,976,989 B1 * | 12/2005 | Vincent ....................... 606/107 |
| 7,014,641 B2 | 3/2006 | Kobayashi et al. |
| 7,025,782 B2 | 4/2006 | Kobayashi et al. |
| 7,033,366 B2 | 4/2006 | Brady |
| 7,037,312 B2 | 5/2006 | Kikuchi et al. |
| 7,074,227 B2 * | 7/2006 | Portney ........................ 606/107 |
| 7,097,649 B2 | 8/2006 | Meyer |
| 7,131,976 B2 | 11/2006 | Kobayashi et al. |
| 7,156,854 B2 | 1/2007 | Brown et al. |
| 7,348,038 B2 | 3/2008 | Makker et al. |
| 7,422,604 B2 | 9/2008 | Vaquero et al. |
| 7,429,263 B2 | 9/2008 | Vaquero et al. |
| 7,458,976 B2 | 12/2008 | Peterson et al. |

| | | |
|---|---|---|
| 7,476,230 B2 | 1/2009 | Ohno et al. |
| 7,494,505 B2 | 2/2009 | Kappelhof et al. |
| 7,645,300 B2 | 1/2010 | Tsai |
| 8,273,122 B2 | 9/2012 | Anderson |
| 8,382,769 B2 | 2/2013 | Inoue |
| 8,460,311 B2 | 6/2013 | Ishii |
| 8,470,032 B2 | 6/2013 | Inoue et al. |
| 8,475,528 B2 | 7/2013 | Ichinohe et al. |
| 2001/0007942 A1 | 7/2001 | Kikuchi et al. |
| 2002/0103490 A1 | 8/2002 | Brady |
| 2002/0151904 A1 | 10/2002 | Feingold et al. |
| 2002/0165610 A1 | 11/2002 | Wadlaock |
| 2002/0193805 A1 | 12/2002 | Ott |
| 2003/0036765 A1 | 2/2003 | Van Noy |
| 2003/0040755 A1 | 2/2003 | Meyer |
| 2003/0050647 A1 | 3/2003 | Brady |
| 2003/0088253 A1 | 5/2003 | Seil |
| 2003/0139749 A1 | 7/2003 | Kikuchi et al. |
| 2003/0181921 A1 | 9/2003 | Jeannin |
| 2003/0195522 A1 | 10/2003 | McNicholas |
| 2003/0212406 A1 | 11/2003 | Kobayashi et al. |
| 2003/0212407 A1 | 11/2003 | Kikuchi |
| 2003/0212409 A1 | 11/2003 | Kobayashi |
| 2004/0111094 A1 | 6/2004 | Meyer |
| 2004/0117012 A1* | 6/2004 | Vincent ................... 623/6.12 |
| 2004/0238392 A1 | 12/2004 | Peterson et al. |
| 2004/0243141 A1 | 12/2004 | Brown et al. |
| 2005/0033308 A1 | 2/2005 | Callahan et al. |
| 2005/0049605 A1 | 3/2005 | Vaquero et al. |
| 2005/0049606 A1 | 3/2005 | Vaquero et al. |
| 2005/0125000 A1 | 6/2005 | Tourrette et al. |
| 2005/0182419 A1 | 8/2005 | Tsai |
| 2005/0222578 A1 | 10/2005 | Vaquero |
| 2005/0261703 A1 | 11/2005 | Feingold et al. |
| 2006/0085013 A1 | 4/2006 | Dusek |
| 2006/0142781 A1 | 6/2006 | Pynson et al. |
| 2006/0167466 A1 | 7/2006 | Dusek |
| 2006/0229633 A1 | 10/2006 | Shepherd |
| 2006/0293694 A1 | 12/2006 | Futamura |
| 2008/0033449 A1 | 2/2008 | Cole et al. |
| 2008/0058830 A1 | 3/2008 | Cole et al. |
| 2008/0086146 A1 | 4/2008 | Ishii et al. |
| 2008/0097459 A1 | 4/2008 | Kammerlander et al. |
| 2008/0221584 A1 | 9/2008 | Downer |
| 2008/0248031 A1 | 10/2008 | Tamatani |
| 2009/0036898 A1 | 2/2009 | Ichinohe |
| 2009/0043313 A1 | 2/2009 | Ichinohe |
| 2009/0112223 A1 | 4/2009 | Downer et al. |
| 2009/0125034 A1 | 5/2009 | Pynson |
| 2009/0138022 A1 | 5/2009 | Tu et al. |
| 2009/0204122 A1 | 8/2009 | Ichinohe et al. |
| 2009/0216244 A1 | 8/2009 | Pynson |
| 2009/0248031 A1 | 10/2009 | Ichinohe |
| 2010/0161049 A1 | 6/2010 | Inoue |
| 2010/0185206 A1 | 7/2010 | Ichinohe |
| 2010/0217273 A1 | 8/2010 | Someya |
| 2010/0286704 A1 | 11/2010 | Ichinohe et al. |
| 2011/0082463 A1 | 4/2011 | Inoue |
| 2011/0098717 A1 | 4/2011 | Inoue |
| 2011/0264101 A1 | 10/2011 | Inoue et al. |
| 2011/0270264 A1 | 11/2011 | Shoji et al. |
| 2011/0288557 A1 | 11/2011 | Kudo et al. |
| 2012/0022549 A1 | 1/2012 | Someya |
| 2012/0071887 A1 | 3/2012 | Ichinohe et al. |
| 2013/0006259 A1 | 1/2013 | Sanger |
| 2013/0018460 A1 | 1/2013 | Anderson |

FOREIGN PATENT DOCUMENTS

| | | |
|---|---|---|
| EP | 0363213 | 4/1990 |
| EP | 0727966 | 9/2003 |
| EP | 1832247 A1 | 9/2007 |
| EP | 1832247 A1 | 9/2007 |
| EP | 1338254 | 12/2008 |
| FR | 2749752 A | 12/1997 |
| JP | 63-197453 A | 8/1988 |
| JP | 4-212350 A | 8/1992 |
| JP | 5-103808 | 4/1993 |
| JP | 5-103809 | 4/1993 |
| JP | 8-024282 A | 1/1996 |
| JP | 8-505540 | 6/1996 |
| JP | 9-506285 A | 6/1997 |
| JP | 11-113939 A | 4/1999 |
| JP | 11-506357 A | 6/1999 |
| JP | 2000-516487 A | 12/2000 |
| JP | 2000-516488 A | 12/2000 |
| JP | 2001-502563 | 2/2001 |
| JP | 2001-104347 A | 4/2001 |
| JP | 2002-516709 A | 6/2002 |
| JP | 2002-355268 A | 12/2002 |
| JP | 2002-541912 A | 12/2002 |
| JP | 2003-144480 A | 5/2003 |
| JP | 3412106 B2 | 6/2003 |
| JP | 2003-210498 A | 7/2003 |
| JP | 2003-325569 A | 11/2003 |
| JP | 2003-325570 | 11/2003 |
| JP | 2003-325572 | 11/2003 |
| JP | 2004-024854 | 1/2004 |
| JP | 2004-188194 A | 7/2004 |
| JP | 2004-351196 A | 12/2004 |
| JP | 2006-181269 A | 7/2006 |
| JP | 2006-297146 A | 11/2006 |
| JP | 2006-333924 A | 12/2006 |
| JP | 2006-333981 A | 12/2006 |
| JP | 2007-503872 A | 3/2007 |
| JP | 2007-152010 A | 6/2007 |
| JP | 2007-181604 A | 7/2007 |
| JP | 2007-526091 A | 9/2007 |
| JP | 2008-521535 A | 6/2008 |
| JP | 2008-212689 A | 9/2008 |
| WO | WO9407436 A1 | 4/1994 |
| WO | WO9513022 A1 | 5/1995 |
| WO | WO9628122 A1 | 9/1996 |
| WO | WO9715253 A1 | 5/1997 |
| WO | WO9812969 A1 | 4/1998 |
| WO | WO0045746 A1 | 8/2000 |
| WO | WO0062712 A1 | 10/2000 |
| WO | WO02071982 A1 | 9/2002 |
| WO | WO02096322 A1 | 12/2002 |
| WO | WO2005023154 A1 | 3/2005 |
| WO | WO2005070341 A1 | 8/2005 |
| WO | WO2005084588 A1 | 9/2005 |
| WO | WO 2006/070628 A1 | 7/2006 |
| WO | WO2006080191 A1 | 8/2006 |
| WO | WO2006090531 A1 | 8/2006 |
| WO | WO2007037223 A1 | 4/2007 |
| WO | WO2007097221 A1 | 4/2007 |
| WO | WO2007080869 A1 | 7/2007 |
| WO | WO2008149794 A1 | 12/2008 |
| WO | WO2008149795 A1 | 12/2008 |
| WO | WO2009058929 A1 | 7/2009 |
| WO | WO2009148091 A1 | 12/2009 |
| WO | WO2011126144 A1 | 10/2011 |
| WO | WO2011155636 A1 | 12/2011 |

* cited by examiner

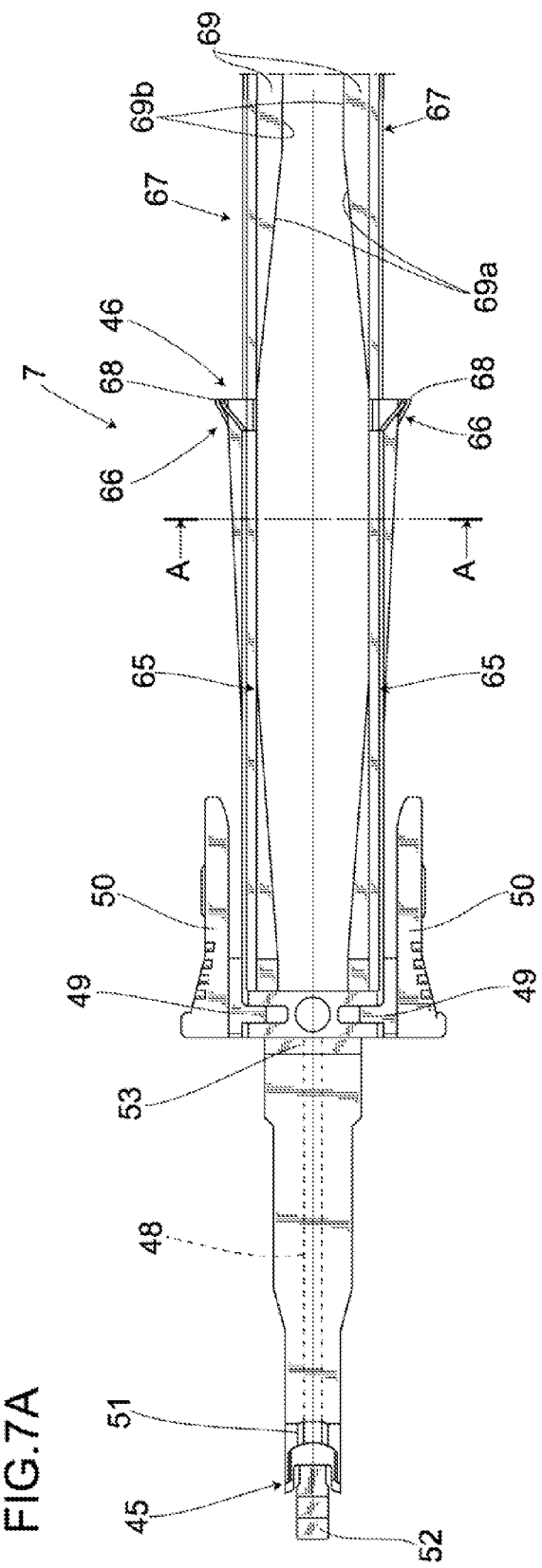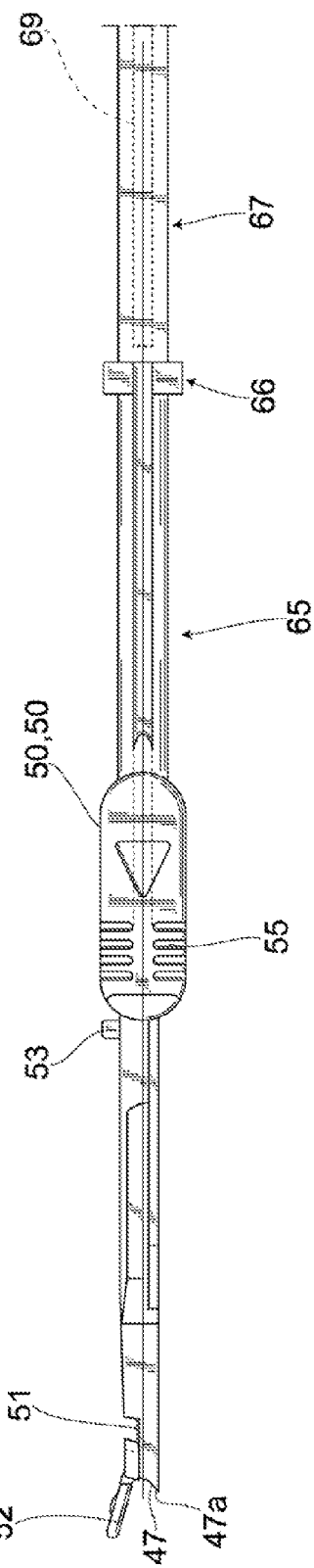

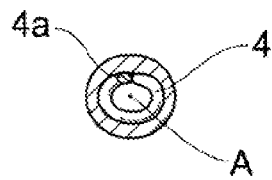
FIG.30E
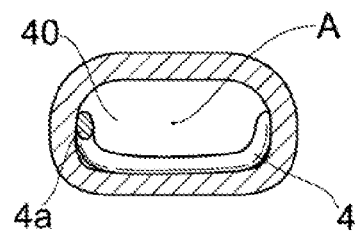
FIG.30D
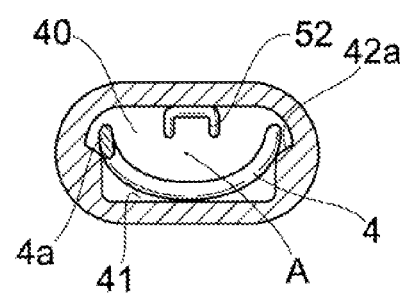
FIG.30C
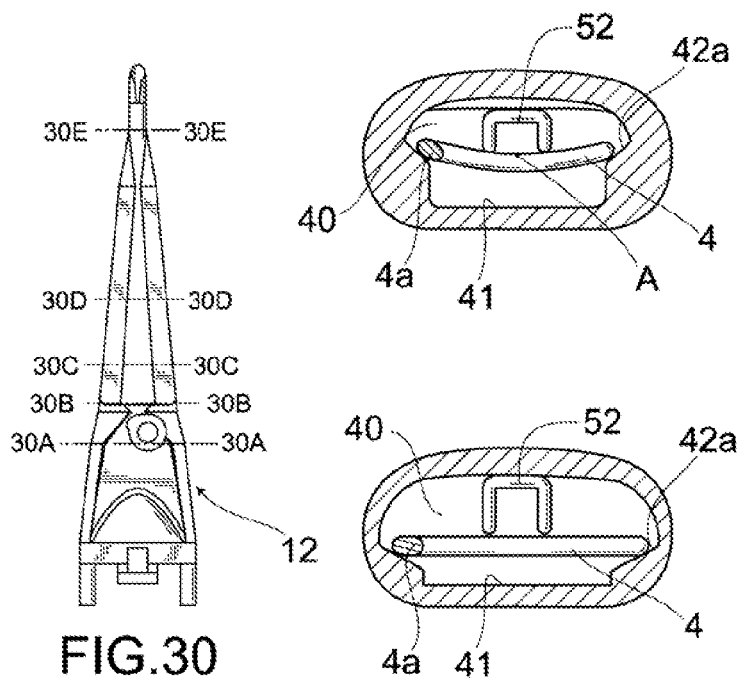
FIG.30B
FIG.30A
FIG.30

INTRAOCULAR LENS INSERTION DEVICE

CROSS-REFERENCE TO RELATED APPLICATIONS

This application is a divisional of U.S. application Ser. No. 12/602,454, having a 371(c) date of Dec. 15, 2009, now U.S Pat. No. 8,475,528 which is the U.S. national stage of PCT application Ser. No. PCT/JP2009/059995, filed May 30, 2008, each of which is incorporated herein by reference in its entirety.

TECHNICAL FIELD

The present invention relates to an intraocular lens insertion device used for inserting an intraocular lens or a phakic intraocular lens into an aphakic eye that has undergone a cataract surgery or a phakic eye in a refractive surgery.

BACKGROUND ART

Elimination of an opacified crystal lens through an ultrasonic emulsification and implantation of a lens into an eye that has undergone the elimination of the crystal lens are commonly carried out in cataract surgeries. Nowadays, using a soft intraocular lens made of a soft material, such as a silicon elastomer or a soft acrylic material, an optical part of the intraocular lens is folded by an intraocular lens insertion device, and the intraocular lens in this state is pushed by a plunger to push out the lens from a nozzle, and is inserted into an eye through an incision which is smaller than the diameter of the optical part.

Intraocular lens insertion devices can insert an intraocular lens into an eye through a tiny incision, thereby reducing the possibilities of a corneal astigmatism or an infection disease after a surgery. To further reduce the possibility of a corneal astigmatism or an infection disease after a surgery, it is desirable to minimize an incision for inserting an intraocular lens into an eye as much as possible.

In order to minimize an incision, however, it is necessary to fold an intraocular lens in a smaller size. Further, it is necessary to fold an intraocular lens in a predetermined shape in order to fix the intraocular lens at a predetermined position in the eye through the small incision.

For solving these problems, it is disclosed that a transition part in which a lens is folded during the movement of an intraocular lens therein has a basal end of an approximately rhombic shape that is gradually deformed into a circular shape at a leading end thereof (For example Patent Document 1).

Patent Document 1: Specification of U.S. Pat. No. 5,275,604

DISCLOSURE OF THE INVENTION

Problem to be Solved by the Invention

According to the above-mentioned Patent Document 1, however, there has been a problem that the transition part is difficult to design and fabricate as a luminal shape of the transition part is complicated.

In view of the forgoing problem, it is an object of the present invention to provide an intraocular lens insertion device which can be easily designed and fabricated.

Means for Solving the Problem

To achieve the above-mentioned object, the intraocular lens insertion device according to a first aspect of the invention is characterized in comprising: a lens disposing part where an intraocular lens is disposed; a slider for pushing out the intraocular lens; a plunger fior further pushing out the intraocular lens pushed out by the slider; a transition part for deforming the intraocular lens pushed out by the slider and the plunger; and a nozzle for ejecting out the deformed intraocular lens, wherein the slider includes: a lens push-out part having a larger contact area than that of the plunger; and a lens holder for pressingly holding one face of an optical part of the intraocular lens relative to one direction, and the transition part deforms portions of an outer edge of the intraocular lens that are parallel to a lens traveling direction relative to an other direction opposite to the one direction.

The invention according to a second aspect of the invention is characterized in that the transition part has a pair of rails parallel to a lens traveling direction and the rails have an inclined face inclined to the other direction as the lens moves to the traveling direction.

Effects of the Invention

According to the intraocular lens insertion device set forth in the first aspect, an intraocular lens can be surely folded into a predetermined shape by pressing an optical part of the intraocular lens through a lens holder and at the same time deforming the outer edge of the intraocular lens into the opposite direction to the one direction through a transition part. Further, the structure is comparatively simple, and hence, it is possible to readily form the intraocular lens insertion device and further to readily mass-produce the same.

According to the intraocular lens insertion device set forth in the second aspect, the intraocular lens can be surely deformed into a predetermined shape only by moving the intraocular lens in the lens traveling direction.

BRIEF DESCRIPTION OF THE DRAWINGS

FIG. 7A is a top plan view showing the structure of a slider and FIG. 7B is a side view thereof;

FIG. 30 is a plan view of the leading end member and FIGS. 30A-30E are partial cross-section views thereof showing the operation of the device step by step;

BEST MODE FOR CARRYING OUT THE INVENTION

Hereinafter will be explained preferred embodiments of the invention with reference to the accompanying drawings.

1. General Structure

Figure 1:
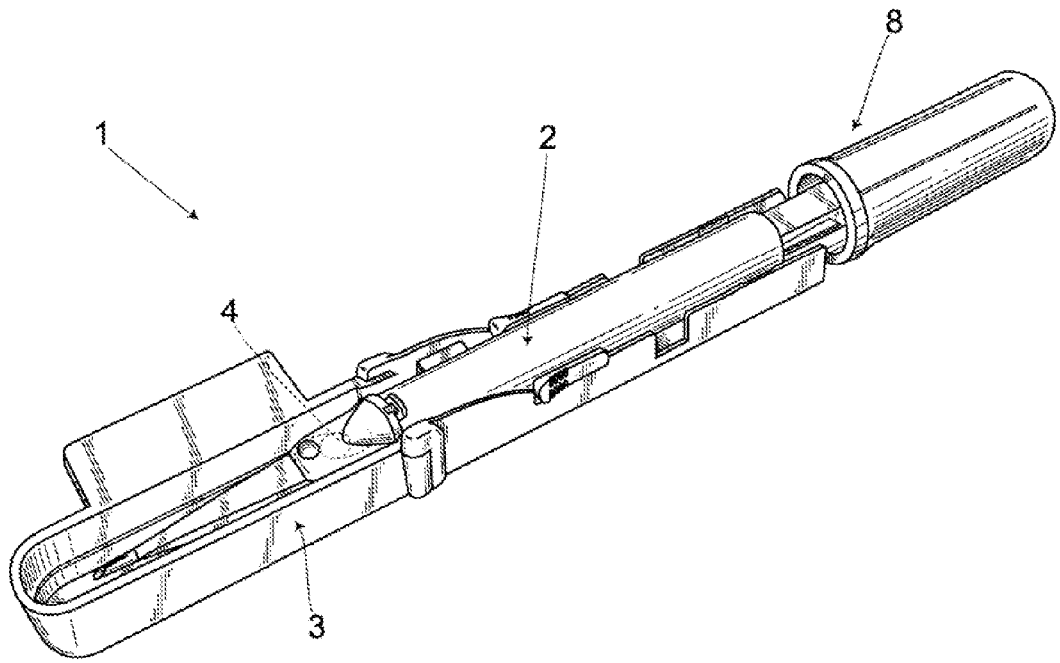
FIG. 1 is a perspective view showing the structure of an intraocular lens insertion device according to an embodiment of the invention.

An intraocular lens insertion device 1 shown in FIG. 1 comprises an intraocular lens insertion unit 2 and a casing 3, and is structured in such a way that the intraocular lens insertion unit 2 in which an intraocular lens 4 is loaded beforehand is placed in the casing 3. The intraocular lens insertion unit 2 is placed in the casing 3 in this manner, thereby preventing the intraocular lens 4 loaded in the intraocular lens insertion unit 2 beforehand from accidentally being ejected out therefrom, and from being damaged during a delivery thereof, and prior to a surgery such as at a presurgery preparation after shipment of the intraocular lens insertion device 1 from a manufacturing factory. Forming the intraocular lens insertion device 1 mainly of a synthetic resin overall facilitates a mass production thereof, thus suitable for a disposal application. Note that in the following explanations, the front of a lens traveling axis as a lens traveling direction is simply called "front", and the rear of the lens traveling axis is simply called "rear".

(1) Intraocular Lens Insertion Unit

Figure 2:
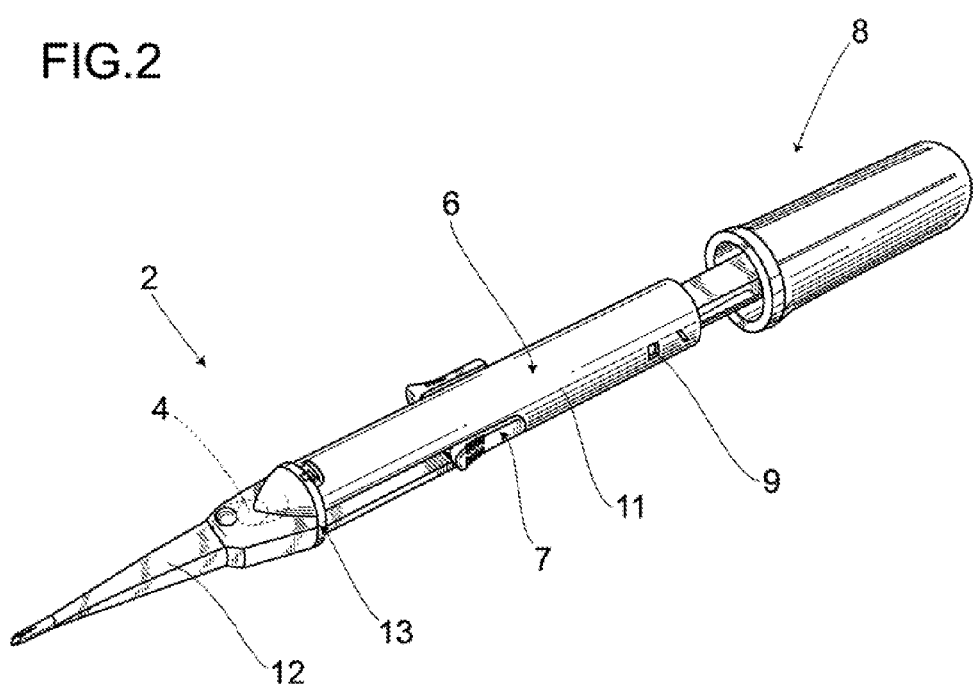
FIG. 2 is a perspective view showing the structure of the intraocular lens insertion device.

As shown in FIG. 2, the intraocular lens insertion unit 2 has a main body 6, a slider 7, a plunger 8, and a lock mechanism 9. The slider 7 and the plunger 8 are provided in such a manner as to move frontward and rearward in the main body 6. The lock mechanism 9 limits a frontward movement of the plunger 8. The lock mechanism 9 is released as the slider 7 is moved frontward, and then the plunger 8 becomes movable frontward. The intraocular lens insertion unit 2 structured in this manner pushes out the intraocular lens 4 by the slider 7 at first, surely folds the intraocular lens 4 in a predetermined shape, and then pushes out the intraocular lens 4 by the plunger 8, folds down the intraocular lens compactly, and inserts the intraocular lens 4 into an eye. Accordingly, the intraocular lens insertion unit 2 causes the lock mechanism 9 to prevent the plunger 8 from pushing out the intraocular lens 4 before the slider 7 pushes out the intraocular lens 4, and folds down the intraocular lens 4 disposed in the main body 6 while moving the intraocular lens 4 frontward through two stages by the slider 7 and then by the plunger 8.

(a) Main Body

The main body 6 comprises a cylindrical basal end member 11 and a tapered leading end member 12. The basal end member 11 and the leading end member 12 are detachably coupled together by a first coupler 13, thus integrated together.

Figure 3A:
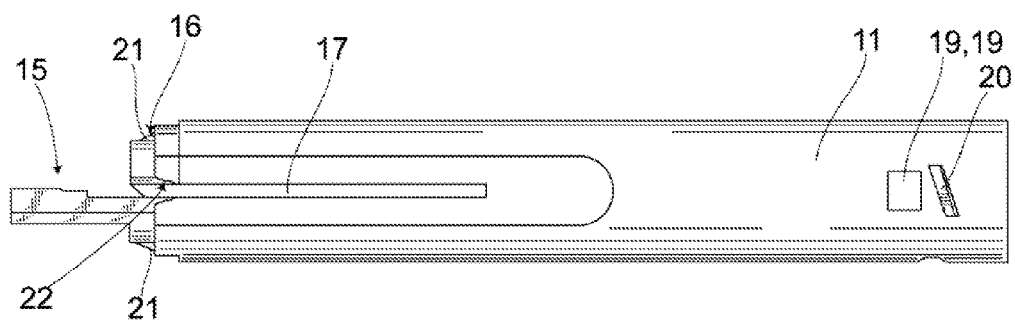
FIG. 3A is a side view showing the structure of a basal end member of the intraocular lens insertion device and FIG. 3B is a cross-sectional view thereof.
Figure 3B:
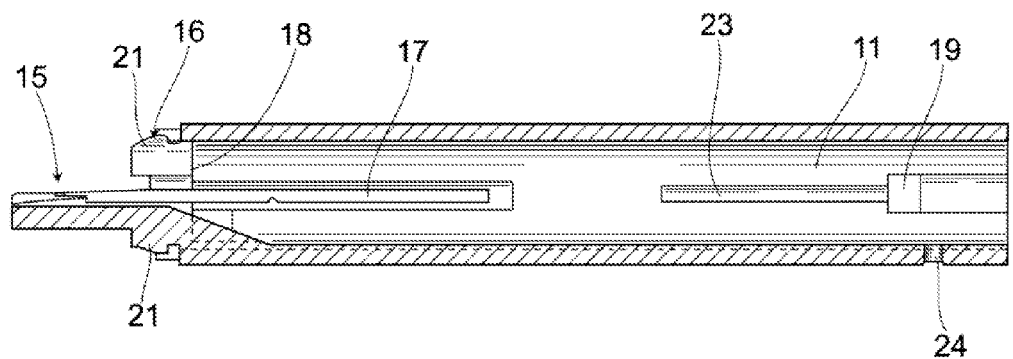

As shown in FIGS. 3A and 3B, the basal end member 11 has a lens disposing part 15, an engagement part 16, slider guides 17, a stopper 18, first latching openings 19, and an engagement protrusion 20.

Figure 4:
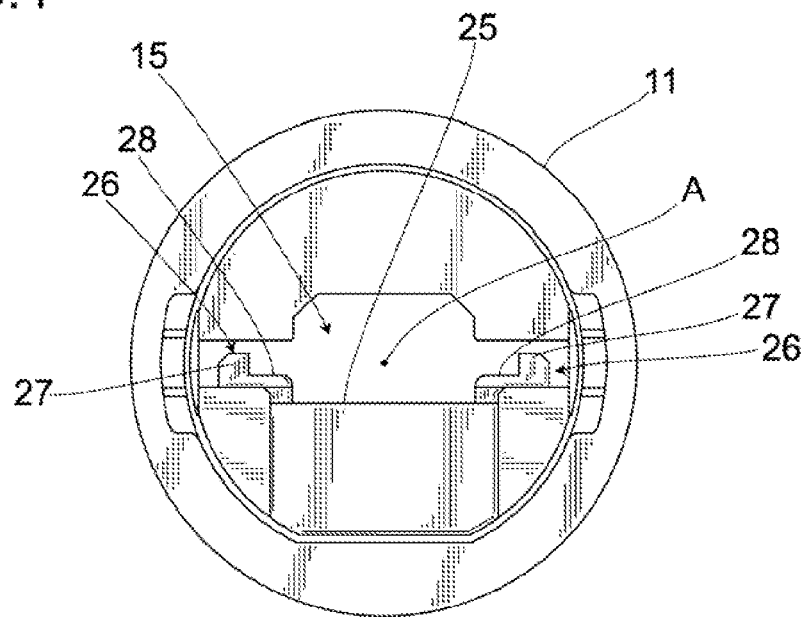
FIG. 4 is a diagram showing the structure of a lens disposing part.

The lens disposing part 15 is formed of a tabular member protruding frontward from a front one end. As shown in FIG. 4, the lens disposing part 15 has a disposing-part bottom face 25 formed horizontal along the lens traveling axis A, and a disposing frame 26 formed at both ends of the disposing-part bottom face 25 parallel to the lens traveling axis A and across the lens traveling axis A. The disposing frame 26 has frame bodies 27, 27 and base end rails 28, 28. Wall-like frame bodies 27, 27 are provided in a standing manner, surrounding the disposing-part bottom face 25 so as to be provided across the lens traveling axis A, and the base end rails 28, 28 are formed integral with the frame bodies 27, 27 in a manner protruding upward of the disposing bottom face 25.

As shown in FIGS. 3A and 3B, the engagement member 16 has first protrusions 21, 21 and widened-part receivers 22, and the first protrusions 21, 21 and the widened-part receivers 22 are provided at the front end of the basal member 11. The two first protrusions 21, 21 are provided in a protruding manner on the outer faces of side walls in a direction orthogonal to the lens traveling axis A. The first protrusions 21, 21 are each formed in a shape like a wedge tapered toward the front. The two widened-part receivers 22 are provided on side walls in a direction orthogonal to the lens traveling axis A and the direction in which the first protrusions 21, 21 are provided. The widened-part receiver 22 is formed by cutting out the side walls of the basal end member 11 so as to be widened toward the front. Accordingly, the first protrusions 21, 21 are provided in a direction orthogonal to the widened-part receivers 22.

The slider guides 17 comprise a pair of slits which are formed in the cylindrical side walls and are parallel to the lens traveling axis A. The slider guide 17 is so formed as to extend from the front end of the basal end member 11 up to the approximate center thereof. The slider guide 17 has the widened-part receiver 22 formed at one end.

The basal end member 11 has the stopper 18 formed on the internal surface of the side wall thereof. The stopper 18 comprises a wall so formed as to plug up a portion of the internal surface of the basal end member 11 at the front end side.

The first latching openings 19 are provided at the other end side which is the rear end side of the basal end member 11, and the two first latching openings 19 are formed in the side walls in the direction orthogonal to the lens traveling axis A. The first latching opening 19 is integrally formed with a latching-part guide 23. The latching-part guide 23 is provided in the internal surface of the side wall, and is constituted by a groove having a bottom surface and running toward the front in parallel with the lens traveling axis A.

The engagement protrusion 20 comprises a part of a thread constituting a male screw formed in such a way that the external surface of the side wall of the basal end member 11 functions as a root of the thread, and is provided on the external surface of the side wall in a direction orthogonal to the lens traveling axis A. The side wall is provided with a second latching opening 24.

Figure 5A:
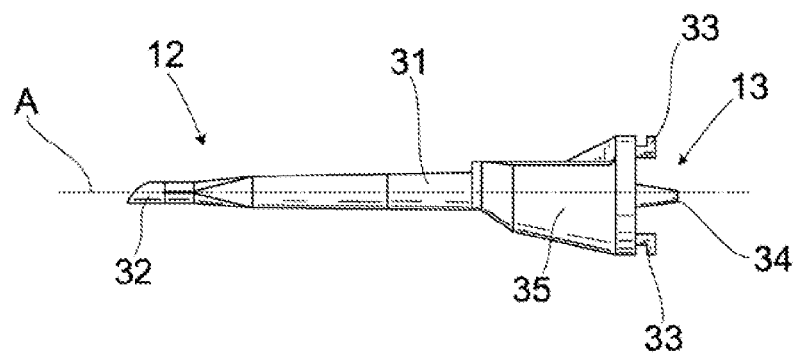
FIG. 5A is a side view showing the structure of a leading end member and FIG. 5B is a cross-sectional view thereof.
Figure 5B:
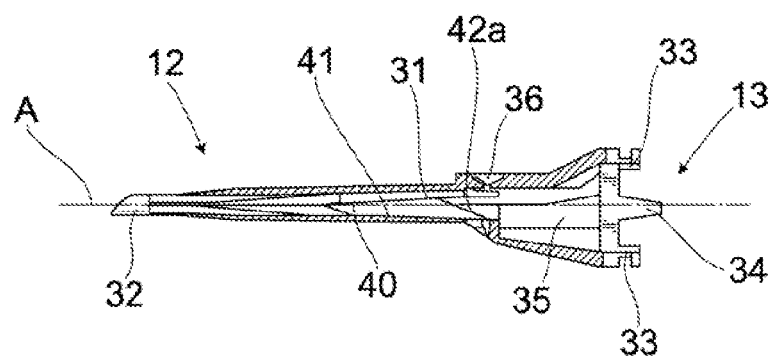

As shown in FIGS. 5A, 5B and 30, the leading end member 12 has the first coupler 13, a transition part 31, and a nozzle 32, and folds up the intraocular lens pushed out from the main body compactly, and ejects out the intraocular lens 4 from the nozzle 32 at the leading end. The leading end member 12 has the first coupler 13 formed at the outer edge of the basal end, and coupled to the main body 6. The leading end member 13 further has the transition part 31 and the nozzle 32 in this order toward the front along the lens traveling axis A.

The first coupler 13 has engagement receivers 33, 33, a widened part 34, and a protective part 35, and couples the leading end member 12 and the main body 6 together. The engagement receivers 33, 33 comprise a pair of openings formed in the base end of the leading end member 12. The opening that constitutes the engagement receiver 33 is formed in a rectangular shape, and is formed in such a manner as to penetrate in a direction orthogonal to the lens traveling axis A.

The widened part 34 is provided in a protruding manner on the base end of the leading member 12 orthogonal to the lens traveling axis and the direction in which the engagement receivers 33, 33 are formed. The widened part 34 comprises a protrusive piece formed in a shape like a wedge tapered toward the rear from the base end.

The protective part 35 is provided between the base end of the leading end member 12 and the transition part 31, and is so formed as to cover the exterior of the lens disposing part 15 of the basal end member 11.

Figure 6:
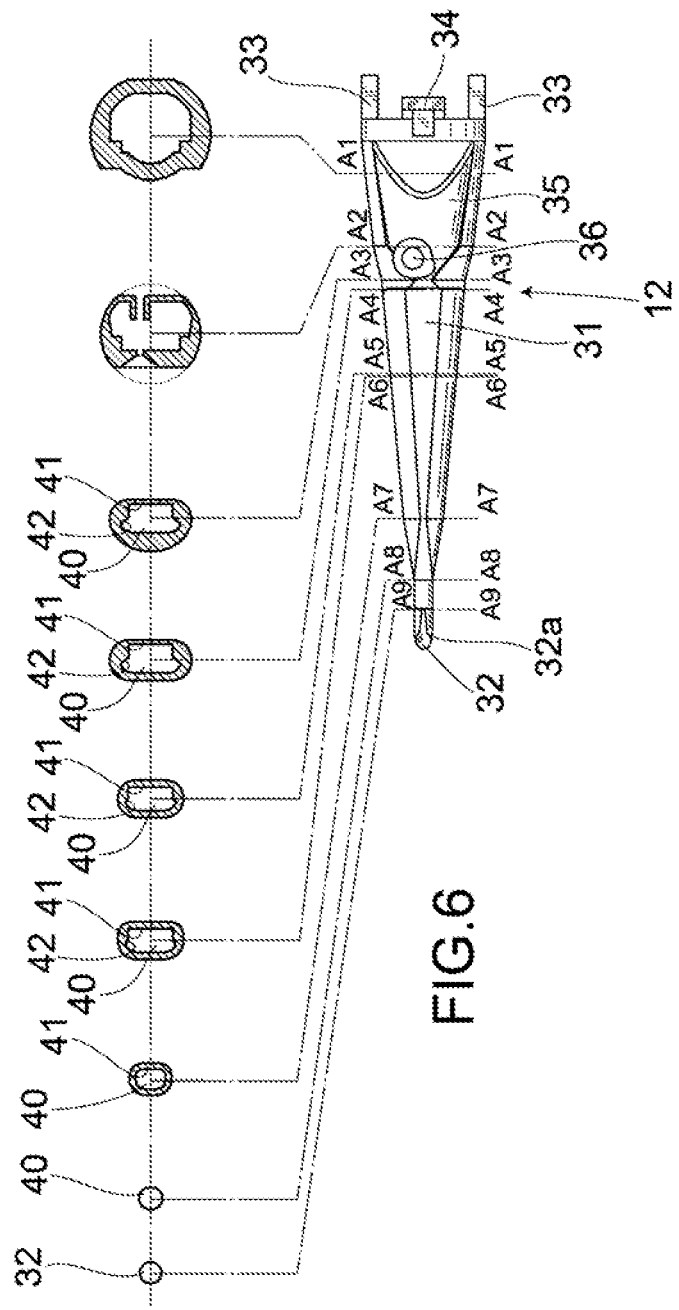
FIG. 6 is a top plan view showing the structure of a transition part with vertical cross-sectional views taken therethrough.

As shown in FIG. 6, the transition part 31 has a lumen 40, a transition-part bottom face 41, and a leading end rail 42 serving as a rail, and folds the intraocular lens 4 disposed on the lens disposing part 15 in a predetermined shape while moving the intraocular lens 4. Note that the rail is so formed as to support portions of the outer edge 4c of the intraocular lens 4 that are parallel to the lens traveling axis A, from beneath.

The lumen 40 is formed in a shape like a mortar that is tapered toward the leading end from the base end. The lumen 40 has the transition-part bottom face 41 and the leading end rail 42 at the bottom thereof.

The transition-part bottom face 41 comprises a tabular member formed horizontally around the lens traveling axis A. The transition-part bottom face 41 is connected to the leading end of a disposing-part bottom face 25 of the basal end member 11, at the basal end of the leading end member 12, which is the rear end thereof. The transition-part bottom face 41 converges into the lumen 40 at the leading end, which is the front end of the leading end member 12.

The leading end rail 42 is formed by causing both sides of the transition-part bottom face 41 to protrude upwardly from the transition-part bottom face 41. The base end which is the rear of the leading end rail 42 matches a part where the protective part 35 and the transition part 31 are connected together. Accordingly, the base end which is the rear end of the leading end rail 42 is connected to the leading ends, which are the front ends of the base end rails 28, 28 provided on the basal end member 11. The leading end rail 42 has an inclined face 42a which inclines upwardly toward the front. The inclined face 42a is formed in the vicinity of the base end of the lumen 40 formed in a shape like a mortar tapered toward the leading end from the base end. The inclined face 42a has a rear base end which holds the intraocular lens 4 in such a way that a portion near the center of the optical part of the intraocular lens 4 does not contact the transition-part bottom face 41, and has a front leading end which has an inclination becoming equal to the height of the center of the height of the lumen 40. Further, the leading end of the inclined face 42a is connected to a parallel plane, and converges gently into the lumen 40 toward the front leading end of the leading end member 12.

The transition part 31 structured as mentioned above has the leading end communicated with the nozzle 32. The nozzle 32 has a circular cross section, and has a leading end formed in a shape inclined downwardly toward the front, and has a slit 32a formed on the top.

Note that the leading end of the inclined face 42a may have a height increased as it converges into the lumen 40 toward the front end without being connected to the parallel plane.

The inclined face 42a of the leading end rail 42 has a certain inclination angle to the transition-part bottom face 41 in FIG. 6, but may be parallel to the transition-part bottom face 41, and in that case, it is desirable that the inclined face 42a should have a height approximately same as that of the base end rail 28 in the vicinity of the basal end member 11, and should gradually increase the height toward the front. The leading end rail 42 may employ a structure of gradually increasing the inclination angle toward the leading end, i.e., having a height approximately equal to that of the base end rail 28 in the vicinity of the basal end member 11, and of gradually inclining inwardly toward the leading end.

The protective part 35 has a through hole 36 opened in a direction orthogonal to the lens traveling axis A and the transition-part bottom face 41. The through hole 36 is provided at that portion where the leading end of the lens disposing part 15 contacts when the basal end member 11 is assembled with the leading end member 12.

(b) Slider

As shown in FIGS. 7A and 7B, the slider 7 has a lens control mechanism 45 and a lock mechanism 46. The lock mechanism 46 prevents the plunger 8 from moving accidentally, and the lens control mechanism 45 moves and deforms the intraocular lens 4 disposed on the lens disposing part 15 as a first stage of a movement and a deformation.

The lens control mechanism 45 has a lens push-out part 47, a guide groove 48, wings 49, 49, operation parts 50, 50, a loop guide 51, a lens holder 52 and a stopper piece 53.

The lens push-out part 47 is constituted by a part of a circular arc having a curvature radius approximately same as the contour of the lens, and is so formed as to contact the intraocular lens 4 surface by surface.

The guide groove 48 is formed in such a way that the plunger 8 can move back and forth along the lens traveling axis A, and the leading end of the plunger 8 can protrude frontward from the lens push-out part 47. The guide groove 48 is constituted by a groove which is formed in one side face of the slider 7 and is parallel to the lens traveling axis A.

The wings 49, 49 are provided on both side faces of the slider 7 across the lens traveling axis A in a protruding manner so as to engage with the slider guides 17. The wings 49, 49 respectively have the operation parts 50, 50 provided integrally with the respective protruding ends thereof. The operation parts 50, 50 are each formed of a tabular member parallel to the lens traveling axis A, and each have a plurality of grooves 55 formed in the external surface in a direction orthogonal to the lens traveling axis A.

The stopper piece 53 is constituted by a wall protruding in a direction orthogonal to the lens traveling axis A, and is provided on the other face side of the slider 7.

The loop guide 51 is formed on the other face side of the leading end of the slider 7 where no guide groove 48 is formed, and is constituted by a groove formed in a planer shape similar to a loop part (to be discussed later) of the intraocular lens 4. The loop part is held in a state where no stress is substantially applied to the internal part of the guide groove 48.

Figure 8:
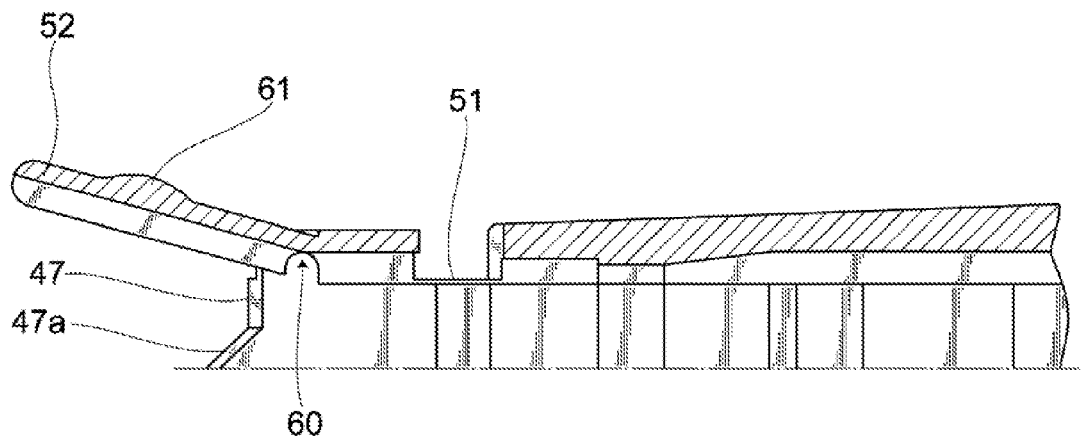
FIG. 8 is a partial enlarged view showing the slider.

As shown in FIG. 8, the lens holder 52 is provided above the lens push-out part 47 so that the lens holder 52 can tilt through a hinge 60. The lens holder 52 is constituted by a member formed in an approximately rectangular shape as viewed from the above, and has a sliding body 61 formed integral on the top face. The sliding body 61 is constituted by a member formed in a shape like a wagon roof extending in a direction orthogonal to the lens traveling axis A, and has a curved face facing upward.

As shown in FIGS. 7A and 7B, the lock mechanism 46 has tilting parts 65, 65, latching parts 66, 66 and extending parts 67, 67. The lock mechanism 46 surely locks the plunger 8 when unused, and surely releases the locking when in use.

The tilting parts 65, 65 are a pair across the lens traveling axis A, and protrude from the respective rear ends of the wings 49, 49 backwardly. The tilting parts 65, 65 are so provided as to tilt on a plane formed by the lens traveling axis A and the tilting parts 65, 65.

Figure 9:
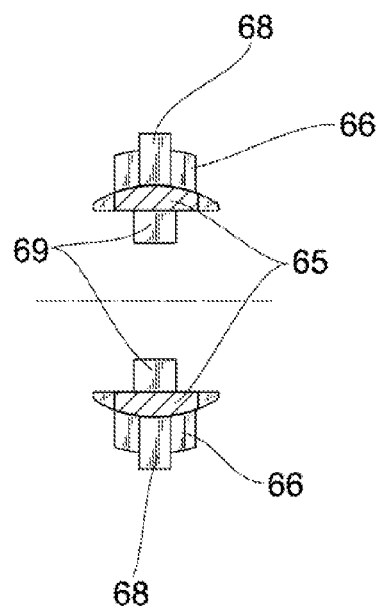
FIG. 9 is a cross-sectional view along a line A-A in FIG. 7A.

The latching parts 66, 66 are formed at the respective center of the tilting parts 65, 65, and are each constituted by a protrusion protruding outwardly, i.e., in a direction away from the lens traveling axis A. The latching part 66 has a tiny protrusion 68 formed at the leading end protruding in the direction away from the lens traveling axis A (see, FIG. 9).

The extending parts 67, 67 are so formed as to protrude backwardly from the respective latching parts 66, 66, and each of which has an urging piece 69 protruding in a direction coming close to the lens traveling axis A (see, FIG. 7A). The urging piece 69 has a connection face 69a inclined inwardly, i.e., inclined so as to come closer and closer from the front of the extending part 67 to the rear thereof. The connection face 69a is connected to a holding face 69b parallel to the lens traveling axis A at the rear of the extending part 67.

(C) Plunger

Figure 10:
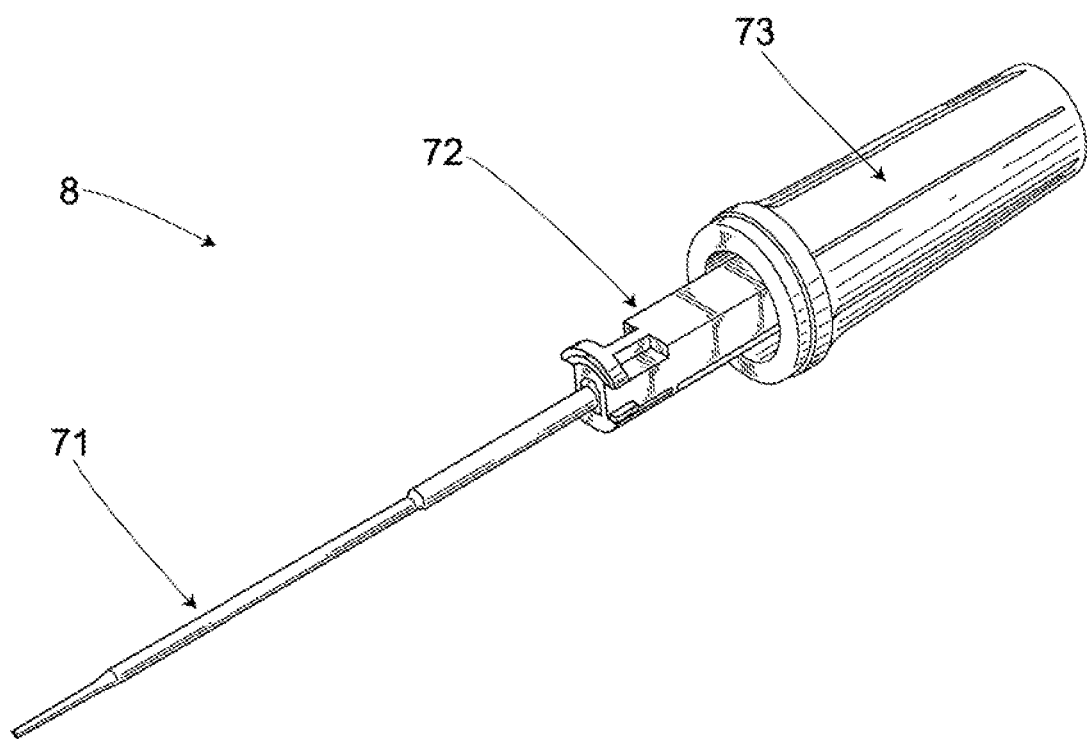
FIG. 10 is a perspective view showing the structure of the slider.

As shown in FIG. 10, the plunger 8 comprises a rod 71, a plunger main body 72, and a grip 73. The plunger 8 performs a second stage of movement and deformation on the intraocular lens 4 moved to some extent and deformed in a predetermined shape by the slider 7. The plunger 8 then inserts the intraocular lens 4 folded up compactly into an eye.

Figure 11:
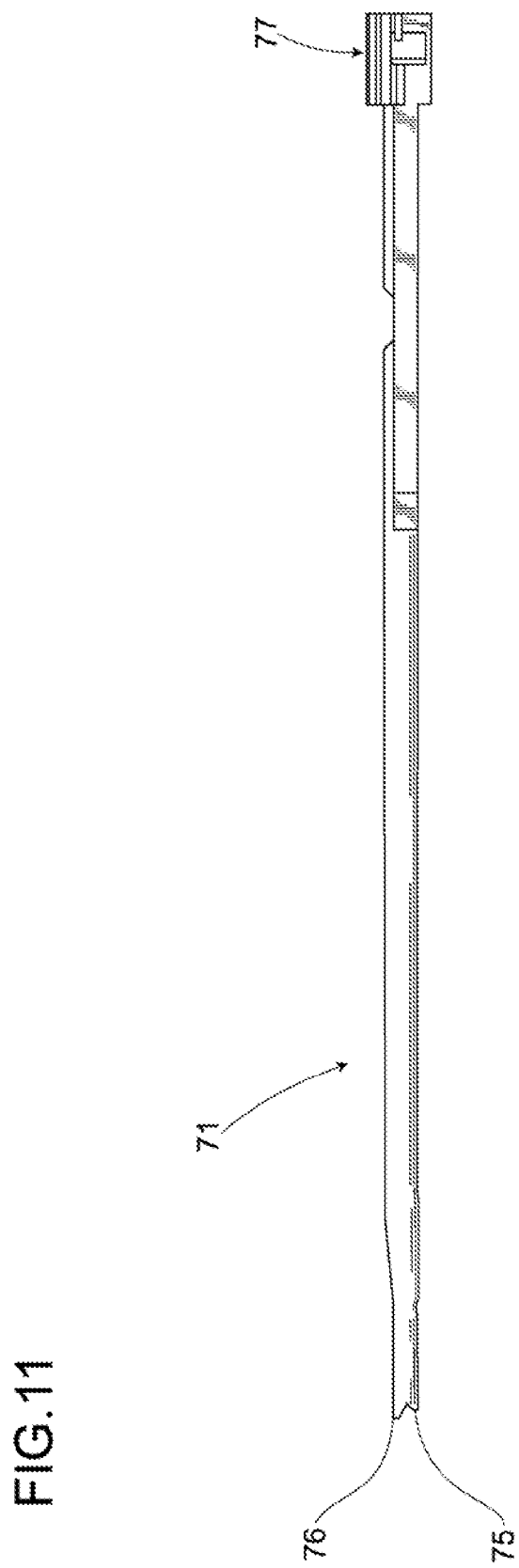
FIG. 11 is a front view showing the structure of a rod.

As shown in FIG. 11, the rod 71 has a rod-like axial part 74 formed in such a way that the one end thereof can protrude from the nozzle 32 of the leading end member 12, and includes a lens contact part 75, a protrusive part 76 and a first attachment part 77.

The lens contact part 75 and the protrusive part 76 are provided at the one end of the rod 71, and are so structured as to contact the outer edge 4c of the intraocular lens 4 that has undergone the first stage of movement and deformation by the slider 7, and then perform the second stage of movement and deformation on the intraocular lens 4. The lens contact part 75 is formed at one side of the front end of the rod 71 and is composed of a plane perpendicular to the lens traveling axis A.

Figure 12:
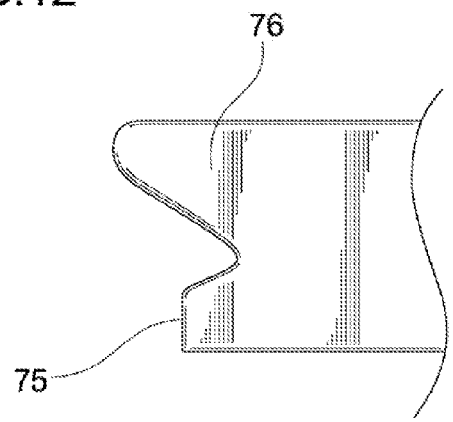
FIG. 12 is a partial enlarged view showing the rod.

As shown in FIG. 12, the protrusive part 76 is pressed in a direction orthogonal to the lens traveling axis A by the intraocular lens 4 pushed out and deformed by the plunger 8. Namely, the protrusive part 76 is so formed as to slide into the overlapped portion of the outer edge of the intraocular lens 4 folded as it travels in the transition part 31. Accordingly, the protrusive part 76 is urged relatively by the thickness to which the outer edge 4c of the intraocular lens 4 is overlapped. Therefore, as the intraocular lens 4 is deformed, the protrusive part 76 is pushed in a direction orthogonal to the lens traveling axis A, i.e., toward the lumen 40 by the intraocular lens 4. The protrusive part 76 is provided on the other side of the front end of the rod 71, and protrudes frontward beyond the lens contact part 75. The protrusive part 76 has an upper face formed in a smoothly and convexly curved face. In this manner, the rod 71 has the lens contact part 75 formed in a direction in which the protrusive part 76 is urged by the intraocular lens 4.

A recess, concaved rearwardly, is formed at the front end of the rod 71 between the lens contact part 75 and the protrusive part 76. This recess is provided to bend the protrusive part 76 when the lens contact part 75 is pushing the intraocular lens 4, and is able to absorb an excessive force applied from the protrusive part 76 to the outer edge 4c of the intraocular lens 4.

Figure 13:
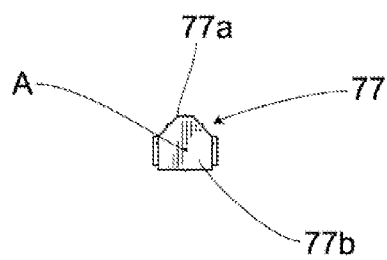
FIG. 13 is a right side view showing the rod.

The rod 71 has the first attachment part 77 provided at the other end of the rod 71 which is the rear end thereof. As shown in FIG. 13, the first attachment part 77 has such a shape that one side of the cross section rises up, and the other end is flat. In this manner, the first attachment part 77 has an asymmetrical cross section with respect to a direction orthogonal to the lens traveling axis A.

Figures 14A, 14B:
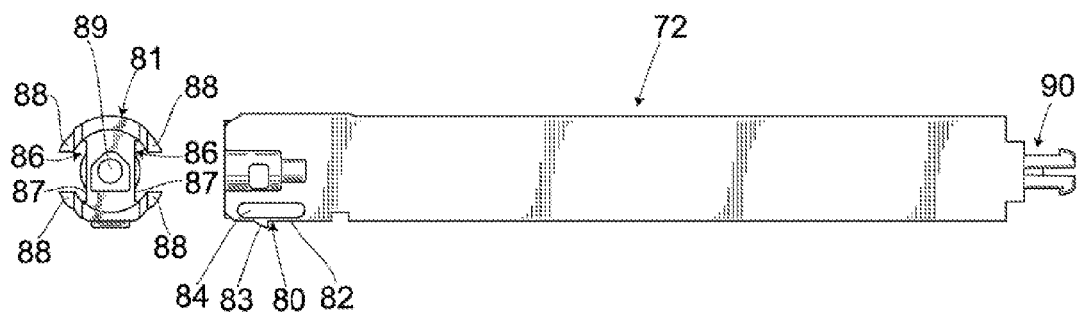
FIG. 14A is a a front view showing the structure of a plunger and FIG. 14B is a left side view thereof.

As shown in FIGS. 14A and 14B, the plunger main body 72 has a second latching part 80 and a circular disk part 81. The second latching part 80 is provided on the front outer face of the plunger main body 72, and is constituted by an elastic piece 82, and a protrusive piece 83 provided on the elastic piece 82. The elastic piece 82 comprises a thin tabular member laid across the face of a hollow 84 formed in the plunger 8.

The circular disk part 81 is formed in a circular shape coaxial with the central axis of the plunger main body 72, and has a pair of release grooves 86, 86 across that central axis. Each release groove 86 has a shape similar to the shape of the latching part 66 as viewed from the direction of the lens traveling axis A, and has a wide bottom face 87 provided in the vicinity of the central axis and second protrusions 88 so formed as to block the bottom face 87 and touch internally the outer edge of the circular disk part 81.

Further, the plunger main body 72 has a first attachment hole 89 formed in the front end thereof, and a second attachment part 90 formed in the rear end.

Figure 15A:
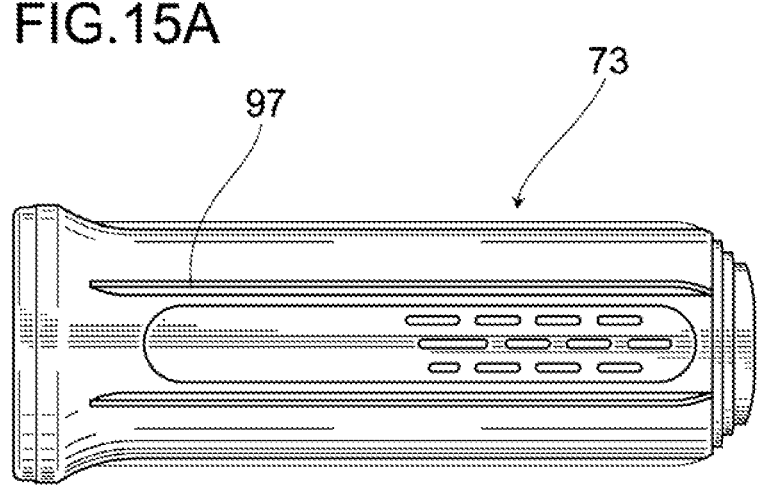
FIG. 15A is a side view showing the structure of a grip and FIG. 15B is a cross-sectional view thereof.
Figure 15B:
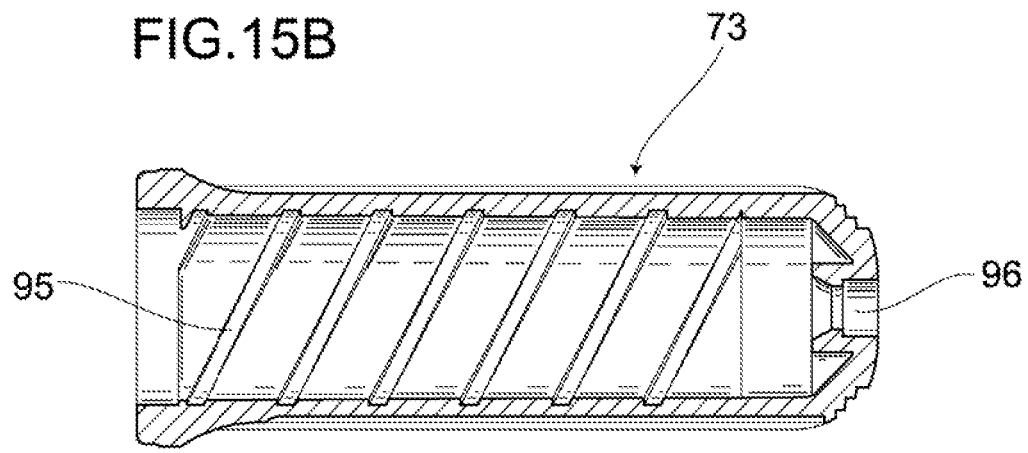

As shown in FIGS. 15A and 15B, the grip 73 is constituted by a member formed in a shape like a cylinder having a bottom. The grip 73 has an internal shape able to be inserted from the rear end of the basal end member 11, and has a female screw 90 formed on the internal surface to engage with an engagement protrusion 20 formed on the outer face of the basal end member 11. The grip 73 has a second attachment hole 96 formed in the center of the bottom face thereof. The grip 73 further has a plurality of antislip protrusive strips 97 formed on the outer face thereof.

(2) Casing

Figure 16:
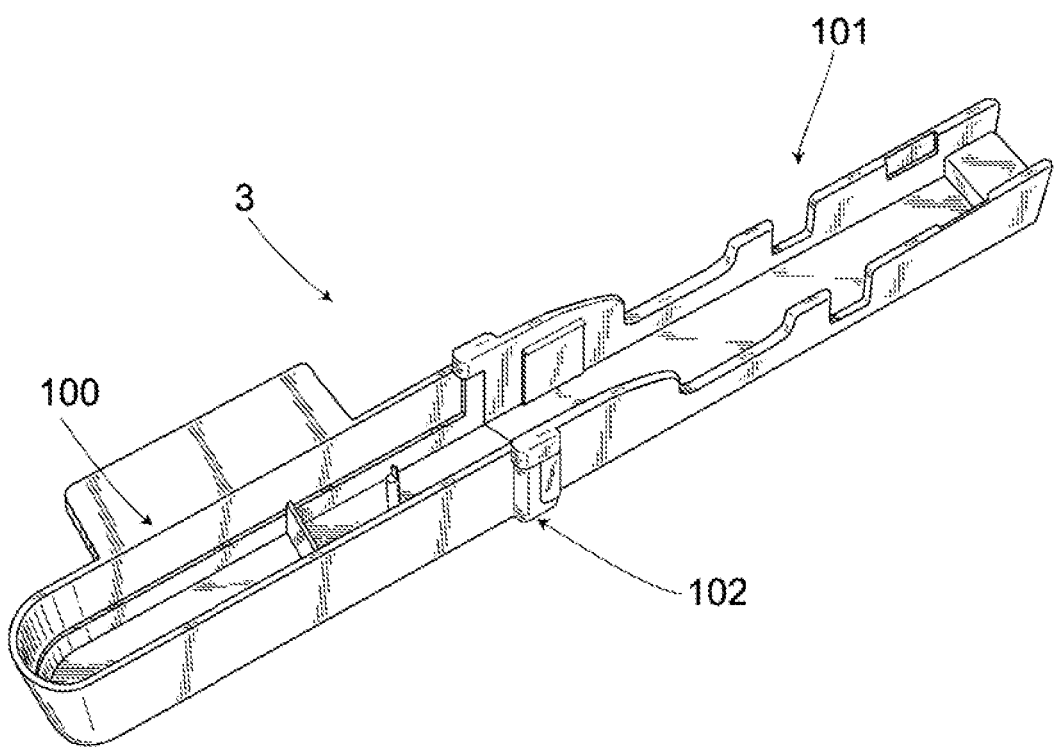
FIG. 16 is a perspective view showing the structure of a casing.

As shown in FIG. 16, the casing 3 is a lengthy box having an opened upper face and a flat bottom face 3a. The casing 3 comprises a case leading end part 100 and a case rear end part 101, both coupled together through a second coupler 102. The casing 3 protects the intraocular lens insertion unit 2 when unused, and holds the intraocular lens 4 disposed beforehand at a predetermined position.

Figure 17A:
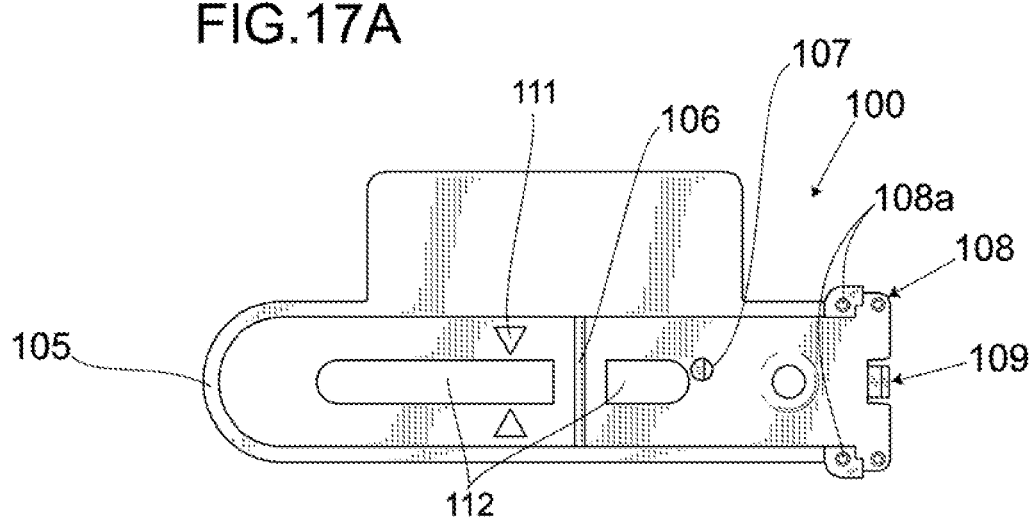
FIG. 17A is a plan view showing the structure of a case leading end.
Figure 17B:
FIG. 17B is a vertical cross-sectional view thereof.
Figure 17C:
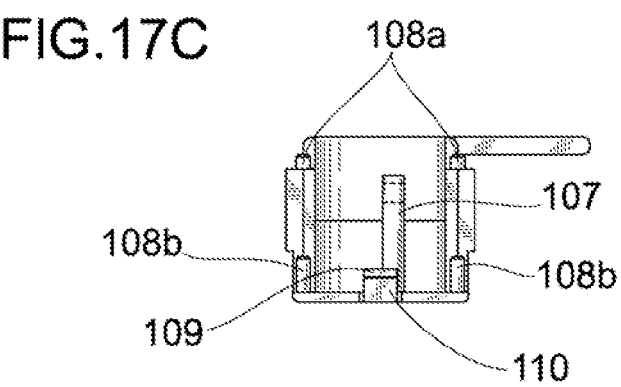
FIG. 17C is an end view thereof.

As shown in FIGS. 17A and 17B, the case leading end part 100 has a protective end 105, a reinforcement piece 106, a holding rod 107, latching rods 108, a latching claw 109, a marking 111, and a gas venting hole 112. The protective end 105 is a standing wall surrounding the one end of the case leading end part 100, and protects the nozzle 32 of the intraocular lens insertion unit 2 attached to the casing 3. The reinforcement piece 106 is a standing wall provided on the internal bottom face 3a of the casing 3, and increases the strength of the casing 3. The holding rod 107 is a cylindrical body provided on the internal bottom face 3a, and has an upper end formed in such a shape that a piece thereof on the protective end 105 side is half removed.

The latching rod 108 and the latching claw 109 are provided at the other end of the opened case leading end part 100. The latching rods 108 are a set of cylindrical bodies protruding in the vertical direction, and have upper latching rods 108a provided at both right and left upper portions of the other end of the case leading end part 100, and lower latching rods 108b provided at both right and left bottom portions of the other end of the case leading end part 100. The length of the lower latching rod 108b in the heightwise direction is longer than the length of the upper latching rod 108a in the heightwise direction. The upper latching rod 108a is formed at a position shifted to the one end side of the case leading end part 100 from the lower latching rod 108b.

The latching claw 109 is provided at a tabular member 110 protruding in the vertical direction from the casing bottom face 3a of the other end of the opened case leading end part 100. The tabular member 110 is elastically deformable.

The marking 111 is provided at a position indicating a proper amount of a lubricant agent in filling the lubricant agent in the intraocular lens insertion unit 2 with the intraocular lens insertion unit 2 being placed in the casing 3. Note that the marking 111 can be marked on the intraocular lens insertion unit 2 itself, but the intraocular lens insertion unit 2 has a limited space for putting the marking 111, so that it is difficult to put a clear marking on the intraocular lens insertion unit 2. In a case where the marking 111 is put on the intraocular lens insertion unit 2, when the intraocular lens 4 is moved in the intraocular lens insertion unit 2, an operator cannot see the moving and deforming intraocular lens 4, thus reducing the operability for the operator. Therefore, it is not suitable to put the marking 111 on the intraocular lens insertion unit 2 itself.

On the other hand, according to the intraocular lens insertion device 1 of the embodiment, the marking 111 is put on the casing 3, so that an operator can clearly become aware of a position indicating the proper amount of the lubricant agent. Because the intraocular lens insertion unit 2 does not have the marking 111, the operator can see the moving and deforming intraocular lens 4 when the intraocular lens 4 moves in the intraocular lens insertion unit 2, thus improving the operability for the operator. The marking 111 can be in various forms, and for example, can be constituted by punch marking, printing, or a protrusive piece.

The gas venting hole 112 is formed through the base bottom face 3a, thus making it possible to smoothly introduce and remove a gas at the time of a gaseous sterilization.

Figure 18A:
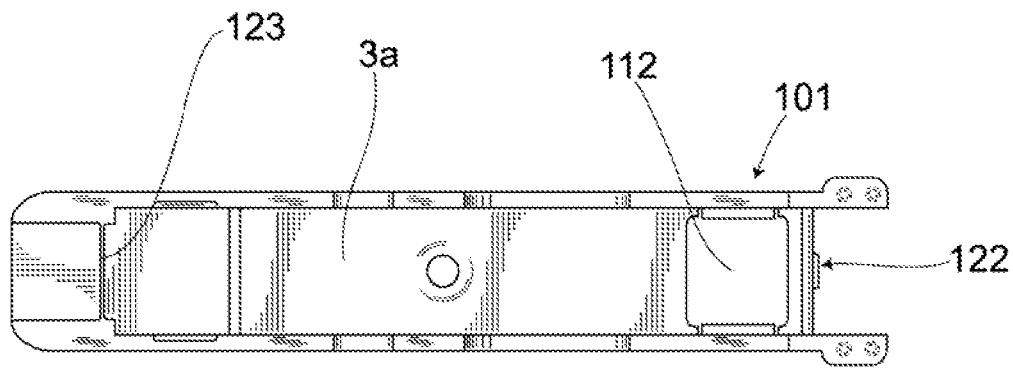
FIG. 18A is a plan view showing the structure of a case rear end.
Figure 18B:
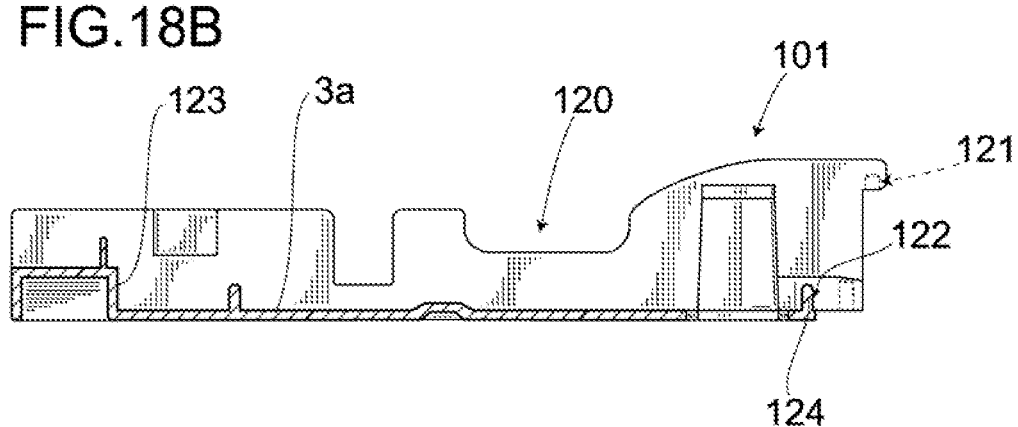
FIG. 18B is a vertical cross-sectional view thereof.
Figure 18C:
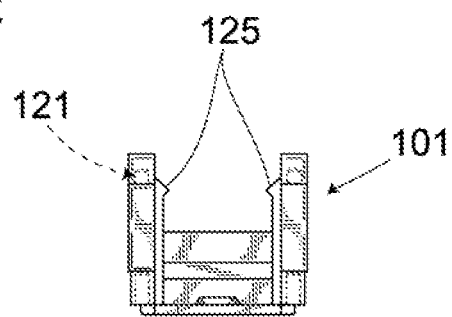
FIG. 18C is an end view thereof.

As shown in FIGS. 18A and 18B, the case rear end part 101 has a locking part 120, third latching holes 121, a claw receiving part 122, and a positioning part 123. The locking part 120 is formed by cutting both side walls so as to substantially correspond to the operation parts 50, 50. The third latching holes 121 are in positions, which are located at an opened end of the case rear end part 101, and correspond to the respective latching rods 108 formed on the case leading end part 100. The positioning part 123 is formed by raising the casing bottom face 3a of the other end of the case rear end part 101 in a vertical direction.

The claw receiving part 122 is provided at a tabular member 124 protruding from the casing bottom face 3a of the opened end of the case rear end part 101 in the vertical direction. The tabular member 124 is elastically deformable.

The case rear end part 101 has detachment preventive parts 125 formed on the internal surfaces of the respective side walls. The detachment preventive part 125 has a protrusion protruding inwardly, and the upper end of the protrusion has a face inclined gently.

2. Assembling Method

Next, an explanation will be given of the method of assembling the intraocular lens insertion device 1 of the invention with reference to the accompanying drawings.

Figure 19:
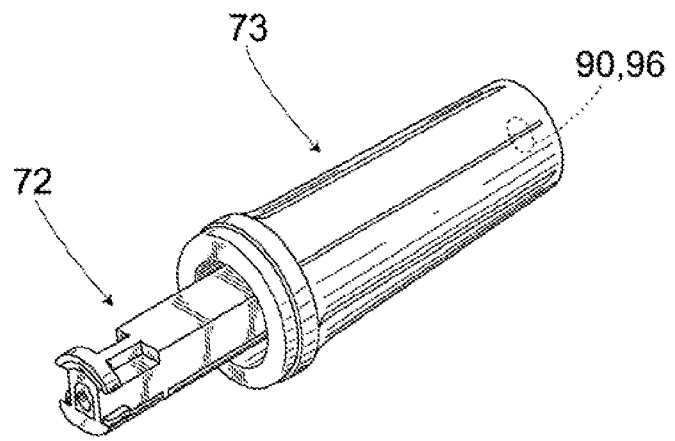
FIG. 19 is a perspective view showing an assembling method step by step.
Figure 20:
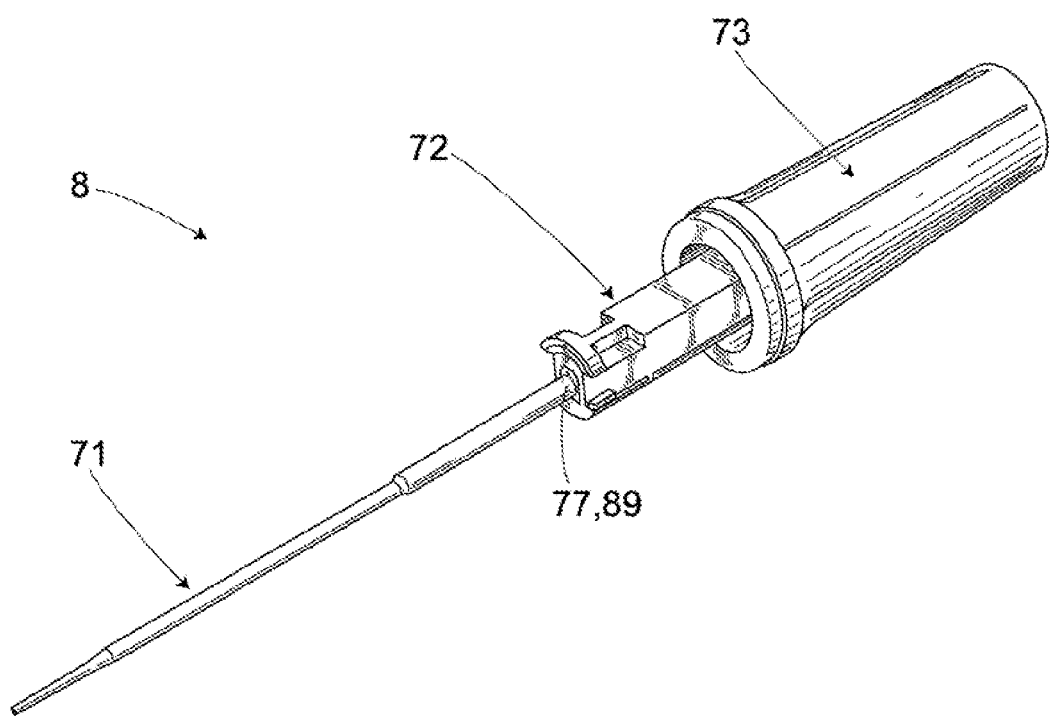
FIG. 20 is a perspective view showing the assembling method step by step.

First, the second attachment part 90 of the plunger main body 72 is fitted into the second attachment hole 96 of the grip 73, thereby coupling the grip 73 and the plunger main body 72 (see, FIG. 19). At this time, the second attachment part 90 is axially supported by the second attachment hole 96. Accordingly, the grip 73 is rotatably supported with respected to the plunger main body 72. Next, the first attachment part 77 of the rod 71 is inserted into the first attachment hole 89 of the plunger main body 72, and fixes the rod 71 to the plunger main body 72 (see, FIG. 20). Because the first attachment part 77 of the rod 71 has a cross section asymmetrical in a direction orthogonal to the lens traveling axis A, the rod 71 can be surely fixed to the plunger main body 72 in a predetermined direction. The grip 73, the plunger main body 72, and the rod 71 are coupled together in this manner, thereby assembling the plunger 8.

Figure 21:
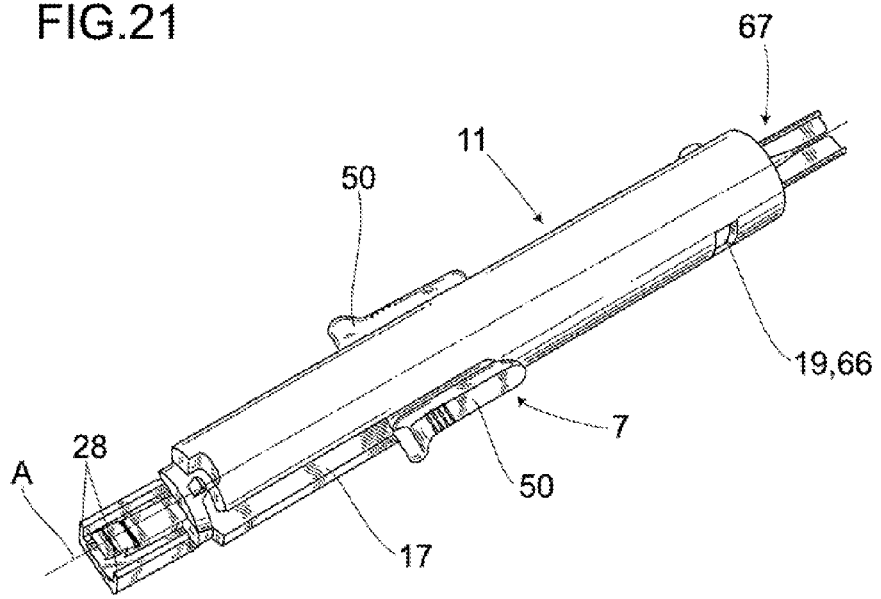
FIG. 21 is a perspective view showing the assembling method step by step.

Subsequently, the slider 7 is attached to the basal end member 11 (see, FIG. 21). To attach the slider 7 to the basal end member 11, one end of the basal end member 11 where the slider guide 17 is formed is widened in the direction orthogonal to the lens traveling axis A, and the extending parts 67, 67 are inserted through the one end to attach the slider 7. The slider 7 is attached in such a way that the direction thereof at this time becomes a direction in which the one end provided with the guide groove 48 faces the lens disposing part 15 of the basal end member 11. The wings 49, 49 are slid in the respective slider guides 17 by holding the operation parts 50, 50, and the slider 7 is slid until the wings 49, 49 reach the ends of the respective slider guides 17. At the same time, the latching parts 66, 66 of the slider 7 latch with the respective first latching holes 19 of the basal end member 11.

Figure 22:
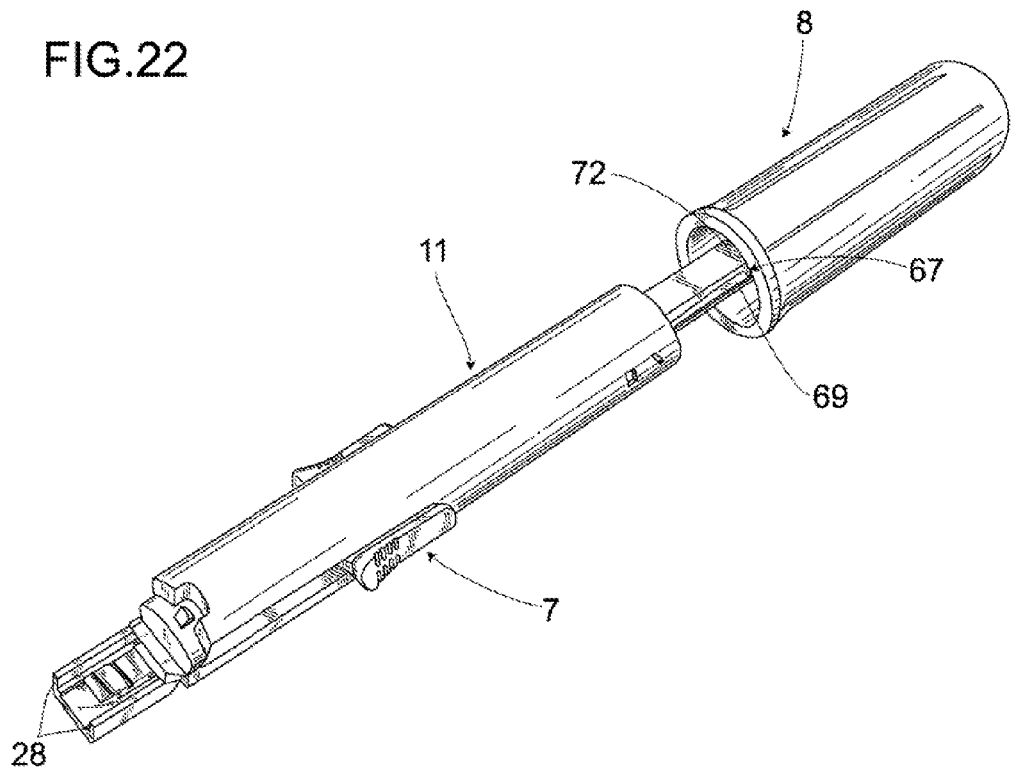
FIG. 22 is a perspective view showing the assembling method step by step.

The plunger 8 is inserted through the other end of the basal end member 11 to which the slider 7 is attached in this manner (see, FIG. 22). At this time, the rod 71 of the plunger 8 is first inserted, and the urging piece 69 of the slider 7 is caused to engage with the release groove 86 formed in the side face of the plunger main body 72. The plunger 8 is inserted until the second latching part 80 of the plunger main body 72 engages with the second latching hole 24 of the basal end member 11.

As explained above, the second latching part 80 is constituted by the elastic piece 82, and the protrusive piece 83 provided on the elastic piece 82, and the elastic piece 82 is a thin tabular member laid across the face of the hollow 84 formed in the plunger 8 in a hanging manner, thus being able to easily deform. Accordingly, by merely inserting the plunger 8 into the basal end member 11, the second latching part 80 can engage with the second latching hole 24, thereby facilitating an assembling of the plunger 8 to the leading end member 12.

The urging piece 69 inclines inwardly from the front of the extending part 67 to the rear thereof, i.e., inclines so as to come close to the lens traveling axis A, and thus as the plunger 8 engages with the guide groove 48, the tilting parts 65, 65 tilt outwardly. As the tilting parts 65, 65 tilt outwardly, the latching parts 66, 66 are urged outwardly, so that the latching parts 66, 66 can be surely engaged with the latching holes of the basal end member 11.

A frontward movement of the plunger 8 is locked because the second protrusions 88 of the circular disk part 81 contact the latching parts 66, 66 of the slider 7.

Figure 23:
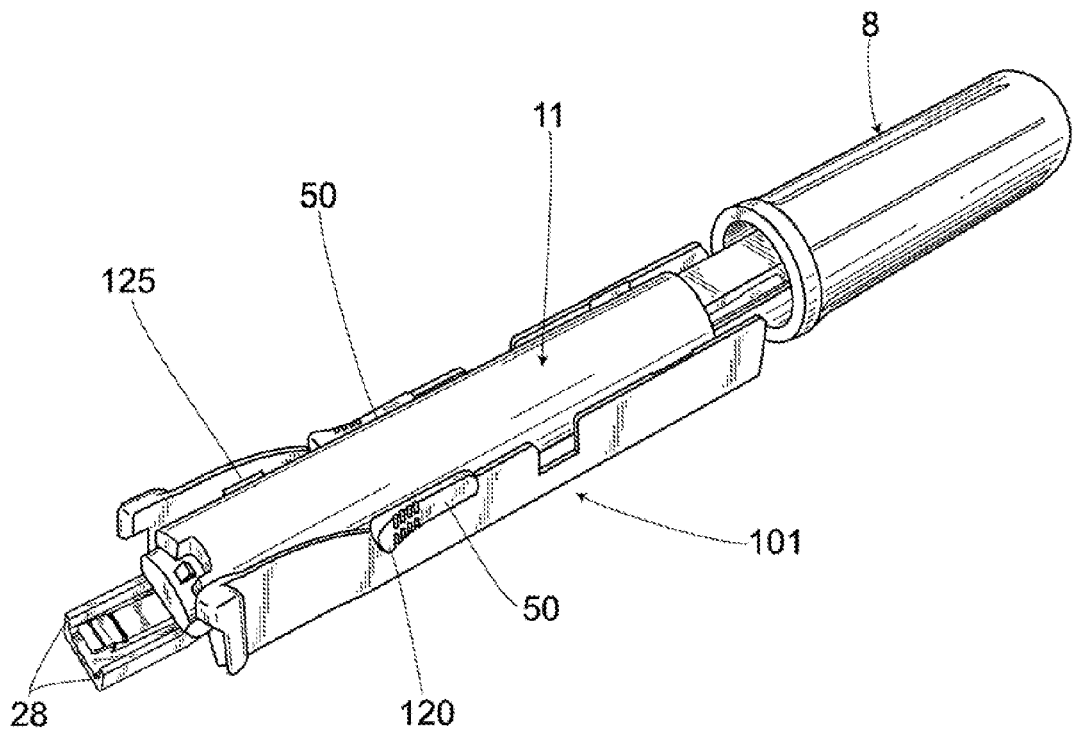
FIG. 23 is a perspective view showing the assembling method step by step.

With the frontward movement of the plunger 8 being locked, the basal end member 11 is placed in the case rear end part 101 (see, FIG. 23). The operation parts 50, 50 are inserted into the lock parts 120, and at the same time, the other end of the basal end member 11 contacts the positioning part 123 of the case rear end part 101. The outer face of the basal end member 11 is engaged with the detachment preventive parts 125 provided on both side walls of the case rear end part 101. The basal end member 11 is placed in the case rear end part 101 in this manner, and the operation parts 50, 50 of the slider 7 are inserted into the lock parts 120 provided in both side walls of the case rear end part 101, thereby locking a frontward or rearward movement of the slider 7.

Figure 24:
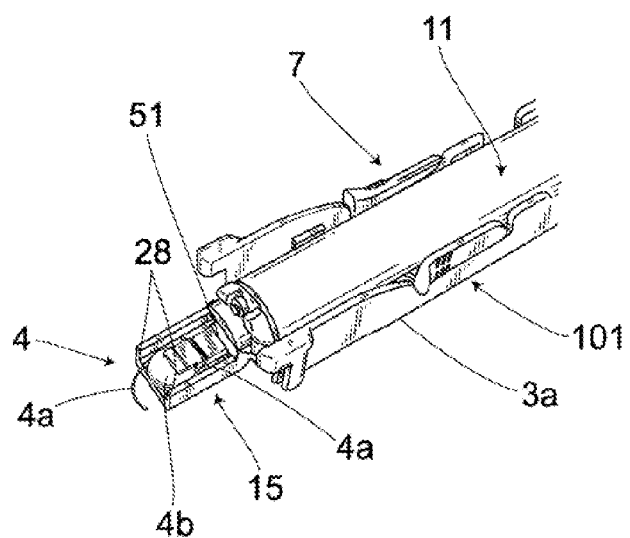
FIG. 24 is a perspective view showing the assembling method step by step.

With the plunger 8 and the slider 7 being locked in this manner, the intraocular lens 4 is disposed on the lens disposing part 15 (see, FIG. 24). The intraocular lens 4 is disposed in such a way that one of a pair of loop parts 4a is positioned at the groove of the loop guide 51 of the slider 7, and the outer edge 4c of the optical part 4b is mounted on the base end rails 28, 28 of the lens disposing part 15. Because the base end rails 28, 28 protrude upwardly from the disposing-part bottom face 25, the intraocular lens 4 can be disposed so as not to have the portion around the center of the optical part 4b contacted by the disposing-part bottom face 25. Therefore, according to the intraocular lens insertion device 1, the intraocular lens 4 can be stored without applying a load to the intraocular lens 4.

According to the embodiment, the intraocular lens 4 is disposed with the basal end member 11 being placed in the case rear end part 101 having the flat casing bottom face 3a. Because the casing 3 is splittable, and one part thereof is attached to the basal end member 11, the basal end member 11 having the lens disposing part 15 can be held in a stable state without any specific jigs, thereby facilitating a disposition of the intraocular lens 4 on the lens disposing part 15.

Figure 25:
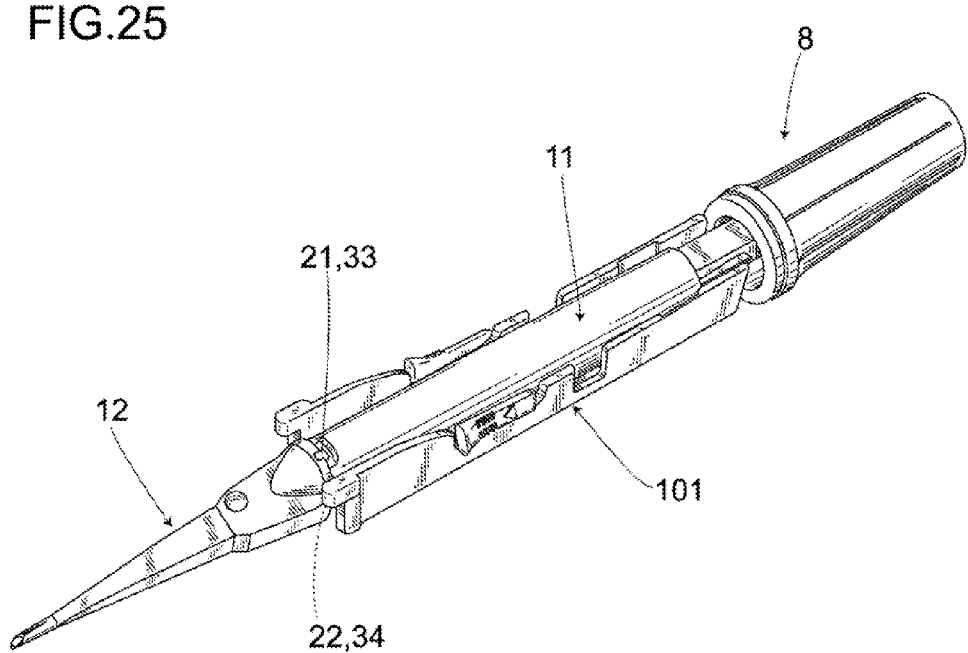
FIG. 25 is a perspective view showing the assembling method step by step.

The engagement part 16 of the basal end member 11 where the intraocular lens 4 is mounted is engaged with the engagement receivers 33, 33 of the leading end member 12, thereby coupling the leading end member 12 and the basal end member 11 together (see, FIG. 25). The leading end member 12 has the widened part 34, and as the widened part 34 is inserted into the widened-part receiver 22 of the basal end member 11, the one end of the basal end member 11 is pushed and widened in a direction orthogonal to the lens traveling axis A and the direction in which the widened-part receiver 22 is provided. Accordingly, the first protrusions 21, 21 of the basal end member 11 provided in a direction orthogonal to the widened-part receiver 22 are caused to bite into the engagement receivers 33, so that the basal end member 11 and the leading end member 12 can be surely coupled together.

By coupling the basal end member 11 and the leading end member 12 together, the disposing-part bottom face 25 of the basal end member 11 and the transition-part bottom face 41 of the leading end member 12 are connected together, and the base end rails 28, 28 of the basal end member 11 and the leading end rail 42 of the leading end member 12 are coupled together.

Because the leading end member 12 is provided with the protective part 35, the intraocular lens 4 disposed on the lens disposing part 15 can be protected.

Figure 26:
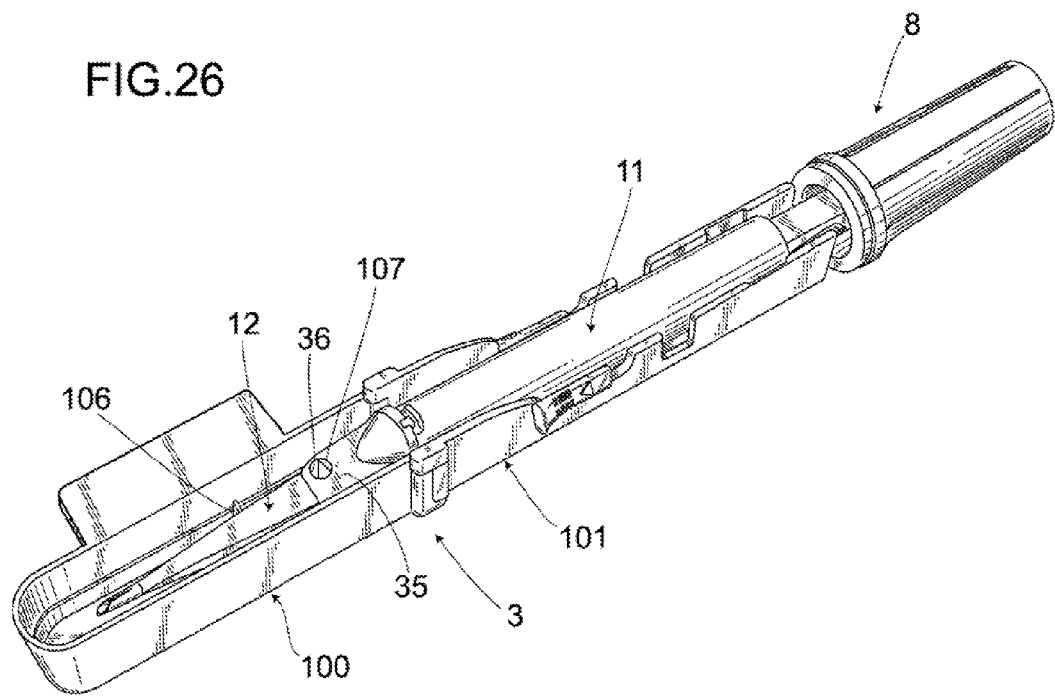
FIG. 26 is a perspective view showing the assembling method step by step.

Subsequently, the latching rod 108 of the case leading end part 100 is inserted into the third latching hole 121 of the case rear end part 101 to do positioning, and the latching claw 109 of the case leading end part 100 is engaged with the claw receiving part 122 of the case rear end part 101 (see, FIG. 26). Note that in a case where positioning is carried out with the four latching rods 108 as in the present embodiment, it is difficult to coincidentally position all four rods to the third latching holes 121.

Figure 27:
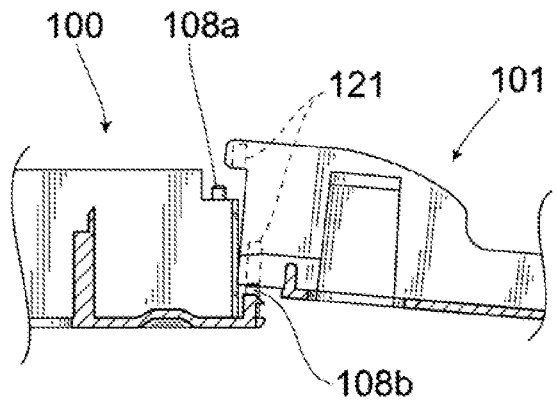
FIG. 27 is a partial cross-sectional view showing the way how the case leading end and the case rear end are coupled together.

On the other hand, according to the embodiment, the latching rod 108 at the case leading end part 100 is formed in such a way that the length of the lower latching rod 108b in the heightwise direction is longer than the length of the upper latching rod 108a in the heightwise direction. Accordingly, the lower latching rod 108b is first inserted into the third latching hole 121, and then the upper latching rod 108a is inserted into the third latching hole 121, thereby enabling a reliable positioning. Namely, changing the lengths of the lower latching rod 108b and the upper latching rod 108a enables the positioning two positions by two positions, thereby remarkably facilitating positioning as compared to by conventional techniques where positioning is carried out on four positions at the same time (see, FIG. 27).

According to the embodiment, because the latching claw 109 is engaged with the claw receiving part 122, the case rear end part 101 and the case leading end part 100 can be surely coupled together. Further, when the latching claw 109 is engaged with the claw receiving part 122, the latching claw 109 makes an engagement sound, thereby preventing an assembling failure like an improper engagement.

The case leading end part 100 has the holding rod 107 provided on the internal bottom face, and the holding rod 107 is inserted into the through hole 36 provided in the protective part 35 of the leading end member 12. The through hole 36 is provided in a position where the leading end of the lens disposing part 15 inserted in the protective part 35 abuts, so that the holding rod 107 prevents the intraocular lens 4 from moving frontward. Therefore, according to the embodiment, the intraocular lens 4 can be surely held at a predetermined position when carried.

3. Working and Effectiveness

Next, an explanation will be given of the working and effectiveness of the intraocular lens insertion device 1 of the embodiment.

First, with the intraocular lens insertion unit 2 being placed in the casing 3 (see, FIG. 26), a viscoelastic material as a lubricant agent is filled in the lens disposing part 15 of the intraocular lens insertion unit 2 through the through hole 36 provided in the leading end member 12.

Because the case leading end part 100 has the marking 111 provided at a position indicating the proper amount of the viscoelastic material, it is easy to fill the viscoelastic material at a proper amount.

According to the intraocular lens insertion device 1, with the intraocular lens insertion unit 2 being placed in the casing 3, the viscoelastic material is filled in the lens disposing part 15 in this manner, and thus it is possible to fill the viscoelastic material with the slider 7 and the plunger 8 being locked and with the nozzle 32 being protected.

Note that the holding rod 107 provided on the case leading end part 100 is inserted into the through hole 36 to prevent the intraocular lens 4 from moving, but because the upper part of the holding rod 107 is formed in such a shape that a piece on the protective part 105 side is half removed, the through hole 36 on the upper part of the leading end member 12 is not plugged by the holding rod 107. Therefore, the viscoelastic material can be surely filled in the lens disposing part 15 through the through hole 36.

When the intraocular lens insertion unit 2 in which the viscoelastic material is filled is removed from the casing 3, the slider 7 becomes movable. Note that the plunger 8 is locked by the lock mechanism 9 so as not to move frontward.

Figure 28:
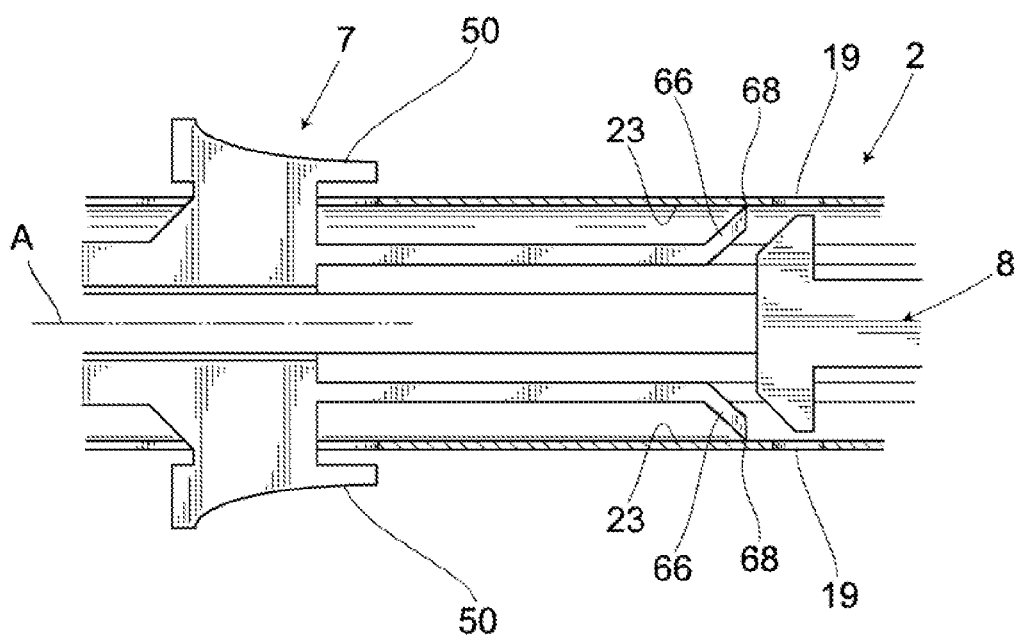
FIG. 28 is a partial cross-sectional view showing the way how the intraocular lens insertion device operates.

The operation parts 50, 50 are grasped, and the slider 7 is moved frontward. As the slider 7 is pushed out, the latching parts 66, 66 abut the internal edges of the first latching holes 19, 19, and the tilting parts 65, 65 tilt inwardly. As the slider 7 is further pushed out, the latching parts 66, 66 pass over the first latching holes 19, 19, and the tiny protrusions 68, 68 provided at the leading ends of the respective latching parts 66 engage with the latching-part guide 23. Then, the engagement of the latching parts 66 and the first latching holes 19, 19 is released, so that the slider 7 can become movable frontward (see, FIG. 28).

Figure 29A:
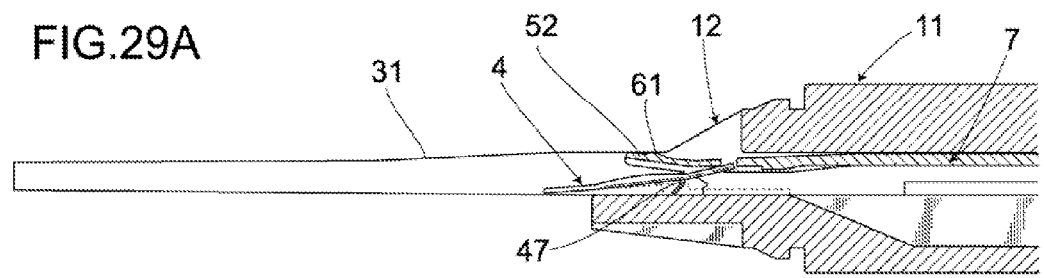
FIGS. 29A-29D are partial cross-section views showing the operation of the device step by step.
Figure 29B:
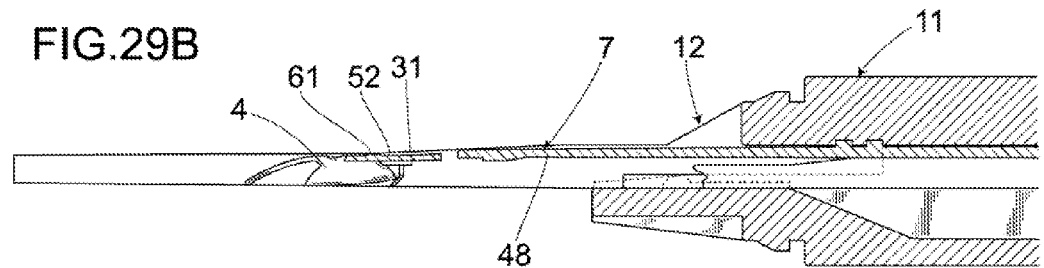

At the leading end of the slider 7, the first stage of movement and deformation is performed on the intraocular lens 4. That is, the lens push-out part 47 of the slider 7 initially abuts the outer edge 4c of the intraocular lens 4 without engaging the geometric center of the lens optical part 4b, and pushes out the intraocular lens 4 (see, FIG. 29A, FIG. 30A). At the same time, the lens holder 52 is pushed against the internal wall of the transition part 31, and swayed downwardly as viewed from a side, and pressingly holds the one face of the optical part of the intraocular lens 4 in a downward direction, which is the one direction (see, FIG. 29B, FIG. 30B).

On the other hand, the intraocular lens 4 moves on the leading end rail 42 that has the inclined face 42a inclined upwardly which is a direction opposite to the direction of pushing the intraocular lens 4 by the lens holder 52, as the intraocular lens 4 moves to the front.

Accordingly, the leading end rail 42 upwardly deforms both sides of the outer edge 4c across the lens traveling axis A, which are portions parallel to the lens traveling direction, in the peripheral edge of the intraocular lens 4, in a direction opposite to the direction in which the intraocular lens 4 is pushed by the lens holder 52 (see, FIG. 30C).

Figure 29C:
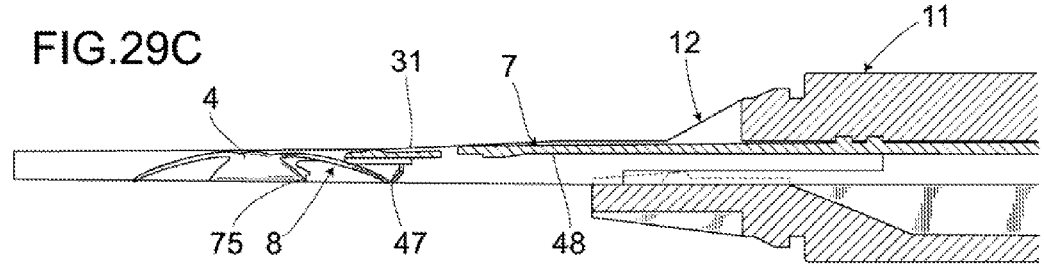

Therefore, according to the intraocular lens insertion unit 2 of the embodiment, the lens holder 52 presses the optical part of the intraocular lens 4 downwardly, while the leading end rail 42 upwardly pushes both sides of the outer edge 4c of the intraocular lens 4 across the lens traveling axis A. Accordingly, the intraocular lens insertion unit 2 can surely fold the intraocular lens 4 in a predetermined shape, i.e., such a shape that the optical part surely protrudes downwardly in the embodiment (see, FIG. 29C and FIG. 30D).

Note that according to the conventional intraocular lens insertion devices, the base end of the transition part is formed in an approximately diamond-like shape, and the leading end thereof is deformed into a circular shape gradually to deform an intraocular lens into a predetermined shape, and hence the shape of the transition part is complex.

In contrast, according to the intraocular lens insertion unit 2 of the embodiment, the leading end rail 42 is provided with the inclined face 42a to deform both sides of the outer edge 4c of the intraocular lens 4 across the lens traveling axis A. Therefore, the shape of the transition part 31 is simplified, thus facilitating the manufacturing of the transition part.

Further, according to the intraocular lens insertion unit 2, the intraocular lens 4 is pushed out by the slider 7 having the lens push-out part 47 which has a larger contact face than the lens contact part 75 of the plunger 8. Accordingly, the intraocular lens insertion unit 2 can push out the intraocular lens 4 without applying local stress.

Still further, the sliding body 61 of the lens holder 52 is formed in a shape like a wagon roof, the sliding body 61 can slide uniformly against the internal wall of the transition part 31, so that it is possible to hold the optical part 4b of the intraocular lens 4 uniformly.

Figure 31:
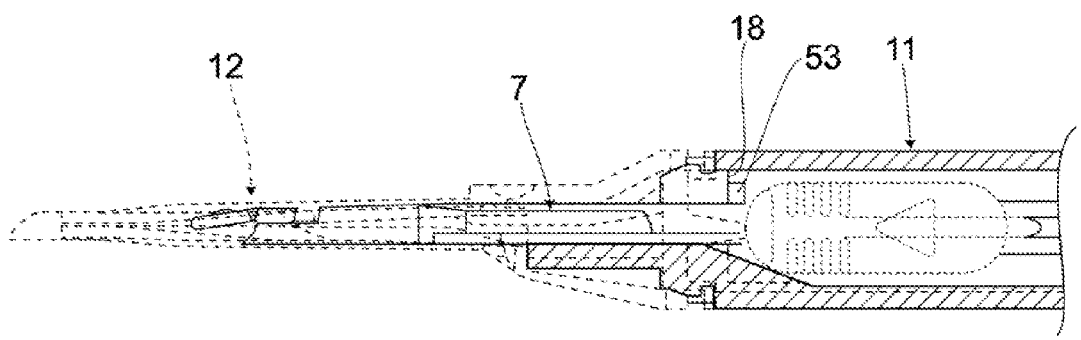
FIG. 31 is a partial cross-sectional view showing the operation.

Yet further, according to the intraocular lens insertion unit 2, because the stopper 18 which abuts the stopper piece 53 of the slider 7 is provided on the basal end member 11, even if the slider 7 is pushed out with strong force, the leading end member 12 does not come apart (see, FIG. 31).

Figure 32:
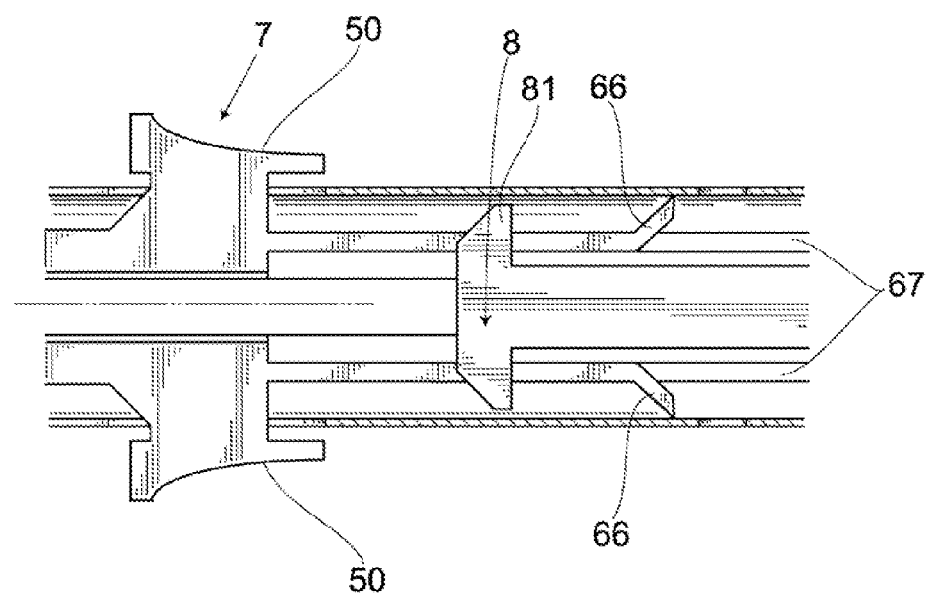
FIG. 32 is a partial cross-sectional view showing the operation.

As the slider 7 is pushed out, locking of the plunger 8 by the lock mechanism 9 is released. That is, as the slider 7 is pushed out, engagement of the latching parts 66, 66 and the second protrusion 88 provided on the circular disk part 81 of the plunger main body 72 are released. Accordingly, the locking of the plunger 8 is released, and the plunger 8 becomes movable frontward while engaging the tilting parts 65 with the release grooves 86, 86 of the circular disk part 81 (see, FIG. 32).

As explained above, because the slider 7 has the extending parts 67, 67, the position of the tilting parts 65 provided on the slider 7 is maintained so as not to be shifted with respect to the release grooves 86 of the plunger main body 72 even when the slider 7 is moved frontward. Therefore, when the slider 7 is moved frontward, the release grooves 86 and the tilting parts 65 can surely engage with one another. Accordingly, it is possible to surely fit the tilting parts 65, 65 into the respective release grooves 86, 86 after the slider 7 is moved, thus ensuring the locking of the plunger 8 to be released, so that the plunger 8 becomes able to be pushed out.

Figure 29D:
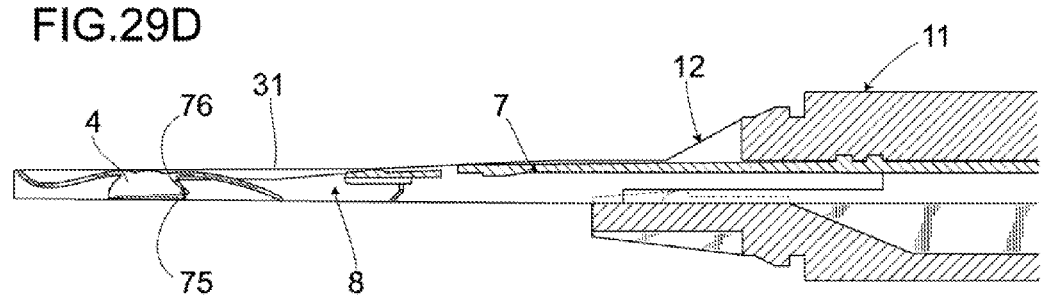

The released plunger 8 performs the second stage of movement and deformation on the intraocular lens 4 deformed in the predetermined shape by the slider 7. That is, as the plunger 8 is pushed out frontward through the guide groove 48 provided in the one side of the slider 7, the lens contact part 75 contacts the outer edge 4c of the intraocular lens 4 deformed in the predetermined shape by the slider 7. The grip 73 is then pushed out, and the female screw 95 is threaded with the engagement protrusion 20 of the basal end member 11. As the grip 73 is rotated in this state, the plunger 8 can be moved to a predetermined extent. As the plunger 8 is moved frontward in this manner, the intraocular lens 4 is further pushed out to the transition part 31, and is folded more compactly (see, FIG. 29D and FIG. 30E). At this time, a sliding resistance applied to the leading end of the rod 71 becomes large.

According to a plunger 8 of the conventional technologies, when the sliding resistance caused by the intraocular lens 4 becomes large to some extent, the leading end of the plunger 8 may run on the optical part of the intraocular lens 4.

In contrast, according to the intraocular lens insertion unit 2 of the embodiment, the rod 71 has the protrusive part 76 formed at the leading end thereof. The protrusive part 76 slides into the overlapped portion of the outer edge 4c of the intraocular lens 4 folded as it travels in the transition part 31. Accordingly, the protrusive part 76 is relatively urged by the thickness to which the outer edge of the intraocular lens 4 is overlapped. Namely, the protrusive part 76 receives force in a direction orthogonal to the lens traveling axis A from the intraocular lens 4 pushed and deformed by the plunger 8, and the force is applied to the lens contact part 75. Then, the lens contact part 75 is pressed downward of the optical part 4b of the intraocular lens 4 by this force. Therefore, even if the sliding resistance becomes large as the intraocular lens 4 is folded compactly, the lens contact part 75 is urged downward of the optical part 4b of the intraocular lens 4, thereby surely preventing the plunger 8 from running on the optical part 4b.

Further, according to the intraocular lens insertion unit 2, the upper face of the protrusive part 76 is formed in a smooth curved shape. Therefore, it is possible to prevent the optical part 4b of the intraocular lens 4 from being damaged due to the upper face of the protrusive part 76. Accordingly, the intraocular lens insertion unit 2 can cause the ejected intraocular lens 4 to achieve a desired characteristic.

Still further, according to the intraocular lens insertion unit 2, the lens contact part 75 is formed by a plane. Accordingly, it is possible to easily position the intraocular lens 4 and the leading end of the plunger 8. Therefore, the intraocular lens insertion unit 2 can surely fold the intraocular lens 4 compactly to eject it.

An intraocular lens insertion device which does not have the foregoing slider 7 can also achieve the above-mentioned effect that a running of the plunger 8 on the optical part 4b of the intraocular lens 4 is surely prevented because the plunger 8 has the protrusive part 76 provided at the leading end thereof. Namely, intraocular lens insertion devices which deform an intraocular lens while moving the intraocular lens by pushing out the intraocular lens disposed at a lens disposing part in a transition part by a plunger may employ a structure of deforming portions of an outer edge of the intraocular lens across a lens traveling axis in a direction orthogonal to the lens traveling axis.

As long as the apparatuses have a function of moving an intraocular lens, intraocular lens insertion devices may be differently structured in such a way that a lens disposing part has a function of the first stage of deformation or an intraocular lens deformed to some extent beforehand may be disposed on a lens disposing part.

Accordingly, the protrusive part slides into an overlapped portion of the outer edge of the intraocular lens folded as it travels in a transition part 31. Thus, because the protrusive part is relatively urged by the thickness to which the outer edge 4c of the intraocular lens is overlapped in this manner, it is possible to prevent the plunger from running on the optical part of the intraocular lens.

This way, the intraocular lens 4 is pushed out by the slider 7 and the plunger 8 from a state where the intraocular lens 4 is disposed on the lens disposing part 15, and is ejected from the nozzle 32 in a state where the intraocular lens 4 is folded compactly.

The present invention is not limited to the foregoing embodiment, and can be changed and modified in various forms without departing from the scope of the invention. For example, the explanation has been given of the case where the lens holder of the slider pushes the optical part of the intraocular lens downwardly and the leading end rail lifts up the peripheral end of the intraocular lens parallel to the lens traveling direction upwardly. The invention is, however, not limited to this case, and the lens holder of the slider may push one face of the optical part of the intraocular lens upwardly, while the leading end rail may deform the peripheral end of the intraocular lens parallel to the lens traveling direction downwardly, which is a direction opposite to the foregoing one direction.

In the foregoing embodiment, although the explanation has been given of the case where the intraocular lens insertion device 1 is mainly formed of a synthetic resin overall, the invention is not limited to this case, and the intraocular lens insertion device 1 may be formed of a metal, such as stainless steel, or titanium.

The invention claimed is:

1. An insertion method for use with an insertion device having a nozzle that is configured to be inserted into an eye, the method comprising the steps of:
   pushing an unfolded intraocular lens, having a lens optic with a geometric center and a lens outer edge, in a first direction relative to the nozzle and toward the nozzle by initially abutting the lens outer edge without initially engaging the geometric center of the lens optic;
   moving diametrically opposed portions of the lens outer edge in a second direction transverse to the first direction as the intraocular lens is being pushed in the first direction; and
   during the moving step, folding the intraocular lens by preventing a portion of the lens optic located between the diametrically opposed portions of the lens outer edge from moving in the second direction by moving a lens holder into contact with the lens optic.

2. An insertion method as claimed in claim 1, wherein the step of pushing an unfolded intraocular lens comprises pushing the unfolded intraocular lens along a lens travelling axis with a slider that is in direct contact with a point on the lens outer edge that is aligned with the lens traveling axis.

3. An insertion method as claimed in claim 2, further comprising the steps of:
   ending pushing of the intraocular lens with the slider; and
   after ending pushing of the intraocular lens with the slider, pushing the folded intraocular lens away from the slider with a plunger that is movable relative to the slider.

4. An insertion method as claimed in claim 1, wherein the step of moving diametrically opposed portions of the lens outer edge comprises:
   positioning the diametrically opposed portions of the lens outer edge on first and second rails, with a gap therebetween, that extend in the second direction; and
   pushing the intraocular lens along the first and second rails.

5. An insertion method as claimed in claim 1, wherein the step of folding the intraocular lens comprises pivoting the lens holder about a hinge into contact with the portion of the lens optic located between the diametrically opposed portions of the lens outer edge.

6. An insertion method, comprising the step of:
   folding an unfolded intraocular lens having a lens optic with diametrically opposed portions, as it is pushed in a first direction through an insertion device, by moving diametrically opposed portions of the lens optic in a second direction that is transverse to the first direction while pivoting a lens holder, that was out of contact with a portion of the lens optic located between the diametrically opposed portions, into contact with the portion of the lens located between the diametrically opposed portions while the lens is being pushed to prevent the portion of the lens located between the diametrically opposed portions from moving in the second direction.

7. An insertion method as claimed in claim 6, wherein the lens optic includes a proximal edge, the method further comprising the step of:
   pushing the unfolded intraocular lens in the first direction with a slider that includes the lens holder, a hinge about which the lens holder pivots, and a push-out part that is adjacent to the hinge and abuts the proximal edge of the lens optic.

8. An insertion method as claimed in claim 7, further comprising the step of:
   pushing the folded intraocular lens in the first direction with a plunger.

9. An insertion method as claimed in claim 7, further comprising the step of:
   pushing the folded intraocular lens in the first direction with a plunger that is movable relative to the slider.

10. An insertion method as claimed in claim 6, further comprising the step of:
    pushing the folded intraocular lens in the first direction with a plunger.

11. An insertion method as claimed in claim 6, wherein the diametrically opposed portions of the lens optic comprise diametrically opposed portions of an outer edge of the lens optic.

12. An insertion method as claimed in claim 6, further comprising the step of:
    pushing the unfolded intraocular lens out of a lens storage region and in the first direction prior to the folding step.

13. An insertion method as claimed in claim 6, wherein moving the diametrically opposed portions of the lens optic in a second direction that is transverse to the first direction comprises moving the intraocular lens while supporting the diametrically opposed portions of the lens optic on spaced first and second rails that extend in a direction generally transverse to the first direction.

14. An insertion method as claimed in claim 6, wherein pivoting a lens holder comprises pivoting the lens holder about a hinge with a tapered surface.

15. An insertion method as claimed in claim 6, further comprising the step of:
    additionally folding the folded intraocular lens with a tapered lumen.

16. An insertion method as claimed in claim 6, wherein the portion of the lens optic located between the diametrically opposed portions comprises the geometric center of the lens optic.

* * * * *